(12) United States Patent
Autran et al.

(10) Patent No.: US 10,485,711 B2
(45) Date of Patent: Nov. 26, 2019

(54) STRAND-BASED LAMINATES IN ABSORBENT ARTICLES

(71) Applicant: The Procter & Gamble Company, Cincinnati, OH (US)

(72) Inventors: Jean-Philippe Marie Autran, Pigeon Forge, TN (US); Urmish Popatlal Dalal, Milford, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 472 days.

(21) Appl. No.: 15/185,050

(22) Filed: Jun. 17, 2016

(65) Prior Publication Data

US 2017/0000659 A1   Jan. 5, 2017

Related U.S. Application Data

(60) Provisional application No. 62/186,404, filed on Jun. 30, 2015.

(51) Int. Cl.
*A61F 13/514*   (2006.01)
*A61F 13/49*   (2006.01)
(Continued)

(52) U.S. Cl.
CPC .. *A61F 13/49012* (2013.01); *A61F 13/15601* (2013.01); *A61F 13/49019* (2013.01); *A61F 13/51464* (2013.01); *A61F 13/51466* (2013.01); *A61F 13/51478* (2013.01); *A61F 13/539* (2013.01); *A61L 15/24* (2013.01); *A61L 15/58* (2013.01); *A61F 2013/49025* (2013.01); *A61F 2013/49093* (2013.01);
(Continued)

(58) Field of Classification Search
CPC .......... A61F 13/49012; A61F 13/49019; A61F 13/51478; A61F 13/5148; A61F 13/51464; A61F 13/51466; A61F 2013/49025; A61F 2013/49026; A61F 2013/49028; A61F 2013/51419
See application file for complete search history.

(56) References Cited

U.S. PATENT DOCUMENTS 4,940,464 A   7/1990   VanGompel et al.
5,092,861 A   3/1992   Nomura et al.
(Continued)

FOREIGN PATENT DOCUMENTS

EP          1256594 A1    11/2002
WO   WO 2007/141745 A2   12/2007
(Continued)

OTHER PUBLICATIONS

13872 PCT International Search Report, dated May 1, 2017, 11 pages.

*Primary Examiner* — Catharine L Anderson
(74) *Attorney, Agent, or Firm* — Charles R. Matson; Kathleen Y. Carter

(57) ABSTRACT

Absorbent articles comprising a multilayer outer cover comprising a first outer layer and a second outer layer comprising a component that exhibits at least partial elastic recovery after mechanical activation in the machine direction; an inner layer, disposed between the first outer layer and the second outer layer, the inner layer comprising elastic strands; and wherein at least one of the first outer layer and second outer layer is laminated to the inner layer.

25 Claims, 16 Drawing Sheets

(51) Int. Cl.
  *A61F 13/15*    (2006.01)
  *A61F 13/539*   (2006.01)
  *A61L 15/24*    (2006.01)
  *A61L 15/58*    (2006.01)
  *B29C 65/00*    (2006.01)
  *B29K 21/00*    (2006.01)
  *B29L 31/48*    (2006.01)

(52) U.S. Cl.
  CPC .............. *A61F 2013/5395* (2013.01); *A61F 2013/53908* (2013.01); *B29C 66/344* (2013.01); *B29K 2021/003* (2013.01); *B29L 2031/4878* (2013.01)

(56) References Cited

U.S. PATENT DOCUMENTS

| | | |
|---|---|---|
| 5,143,679 A | 9/1992 | Weber et al. |
| 5,167,897 A | 12/1992 | Weber et al. |
| 5,246,433 A | 9/1993 | Bridges et al. |
| 5,569,234 A | 10/1996 | Ashton |
| 5,897,545 A | 4/1999 | Kline et al. |
| 5,957,908 A | 9/1999 | Kline et al. |
| 6,120,487 A | 9/2000 | Ashton |
| 6,120,489 A | 9/2000 | Johnson et al. |
| 6,169,151 B1 | 1/2001 | Waymouth et al. |
| 6,518,378 B2 | 2/2003 | Waymouth et al. |
| 6,555,643 B1 | 4/2003 | Rieger |
| 6,559,262 B1 | 5/2003 | Waymouth et al. |
| 6,590,136 B1 | 7/2003 | Young et al. |
| 6,830,800 B2 | 12/2004 | Curro et al. |
| 6,843,134 B2 | 1/2005 | Anderson et al. |
| 6,964,720 B2 * | 11/2005 | Schneider ......... A61F 13/15593 156/161 |
| 7,062,983 B2 | 6/2006 | Anderson et al. |
| 7,223,818 B2 | 5/2007 | Autran |
| 7,776,771 B2 | 8/2010 | Autran |
| 8,168,853 B2 | 5/2012 | Auran et al. |
| 8,182,456 B2 | 5/2012 | Autran et al. |
| 8,445,744 B2 | 5/2013 | Autran et al. |
| 9,072,632 B2 | 7/2015 | Lavon et al. |
| 9,289,332 B2 | 3/2016 | Wade et al. |
| 9,326,899 B2 | 5/2016 | Zink et al. |
| 2003/0233082 A1 | 12/2003 | Kline et al. |
| 2005/0215963 A1 | 9/2005 | Autran et al. |
| 2005/0215964 A1 | 9/2005 | Autran et al. |
| 2006/0121252 A1 | 6/2006 | Lightcap et al. |
| 2007/0287348 A1 | 12/2007 | Autran et al. |
| 2007/0287982 A1 | 12/2007 | Autran et al. |
| 2007/0287983 A1 | 12/2007 | Autran et al. |
| 2008/0045917 A1 | 2/2008 | Autran et al. |
| 2009/0258210 A1 | 10/2009 | Autran et al. |
| 2009/0264844 A1 | 10/2009 | Autran et al. |
| 2010/0040826 A1 | 2/2010 | Autran et al. |
| 2013/0211363 A1 * | 8/2013 | LaVon ............. A61F 13/49012 604/385.3 |
| 2013/0306226 A1 | 11/2013 | Zink et al. |

FOREIGN PATENT DOCUMENTS

| | | |
|---|---|---|
| WO | WO 2010/101998 A2 | 9/2010 |
| WO | WO 2013/090519 A1 | 6/2013 |

* cited by examiner

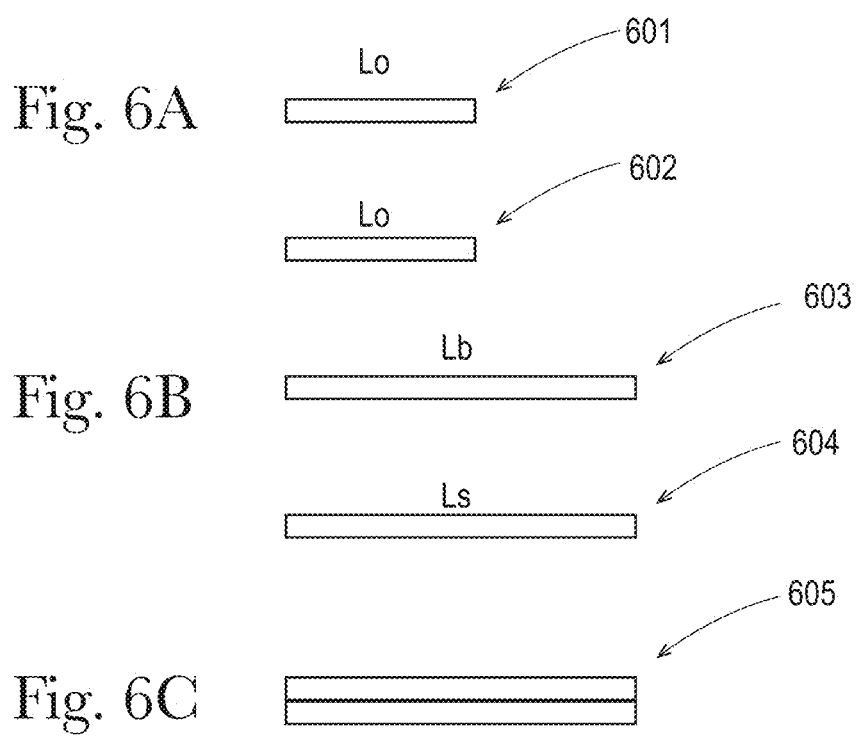

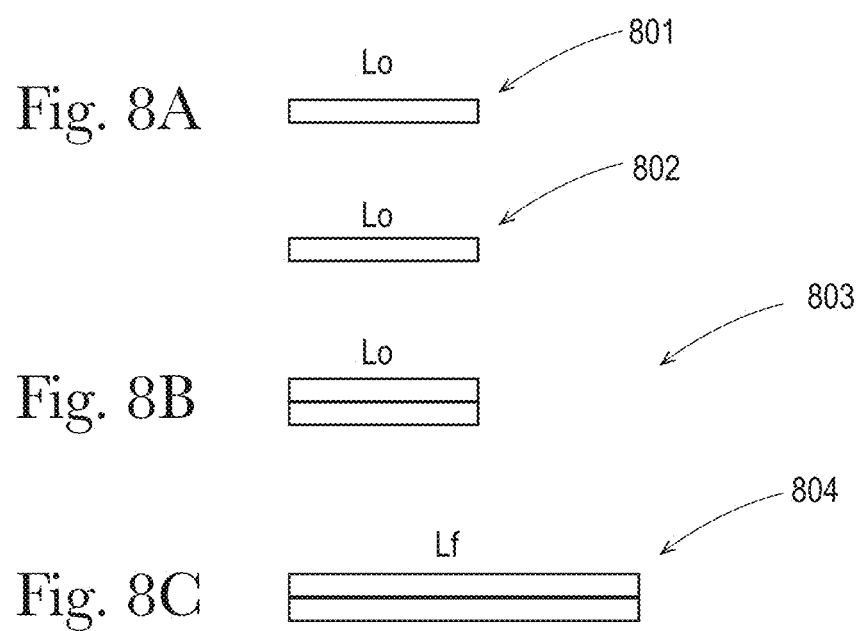

STRAND-BASED LAMINATES IN ABSORBENT ARTICLES

FIELD OF THE INVENTION

The present invention relates to stretch laminates useful for incorporation into absorbent articles.

BACKGROUND OF THE INVENTION

Infants and other incontinent individuals wear disposable absorbent articles such as diapers to receive and contain urine and other body exudates. Training pants or pull-on diapers have become popular for use on children able to walk and often who are toilet training. Many disposable pull-on garments use elastic elements secured in an elastically contractible condition in the waist and/or leg openings. Typically, in order to insure full elastic fit about the leg and the waist such as is provided with durable undergarments, the leg openings and waist opening are encircled at least in part with elasticized bands of rubber or other materials positioned along the periphery of the respective opening.

Stretchable laminates structures used in the chassis of absorbent products and known in the art are for the great majority constructed by using prestrained elastic materials that are adhesively bonded onto two standard nonwoven layers. The elastic material may be, for example, strands, strips of elastic film, or tapes of elastic film. This is often referred to as "live stretch". When fully strained, the elastic-based structures may need to provide stretch up to 120% or to 200%, depending on location, for example, if used in stretch back ears in taped products or in side panels in pant products. However when used as a chassis component that circles around the body and provides 360 degree all-around stretch, 80-170% stretch can suffice. In order to achieve this amount of stretch, the elastic, such as strands or tapes of elastic film, must be prestrained to a higher amount before the nonwoven is bonded onto them. As the nonwovens are applied onto the prestrained strands, the nonwovens form gathered structures as they are forced to accommodate the recovery of the strands. This produces an expansion of the laminates in the direction perpendicular to the plane defined by the strands. The above phenomenon is often referred to as gathering or puckering of the web. The more bonding of the strands and the webs together, the more this constriction takes place during the recovery process.

While these structures and the resulting puckering have been generally accepted by consumers short of alternatives, it has become clear that from a performance standpoint, large amounts of puckering have an undesirable effect to the touch and feel of the final laminates. It also makes it very difficult to create a garment-like look when used in a chassis, which is an ever more desirable feature sought by the consumers.

From a cost standpoint, there are also several negatives: (i) as the nonwovens gather, their basis weight increases and therefore the nonwoven cost increases. For instance, for nonwoven layers applied onto 150% pre-stretched strands or tapes, there is a 250% basis weight increase of the nonwoven layers concomitant with a 250% increase in cost. So 12 grams per square meter (gsm) becomes 30 gsm after gathering with a concomitant increase in cost; (ii) bonding nonwovens together along with elastic strands or tapes strapped in between is extremely inefficient and requires a large amount of adhesive as a lot of adhesive diffuses into the nonwoven itself and becomes ineffective. About 16-20 gsm of adhesive is generally needed; (iii) printing on a nonwoven is neither easy nor cost-effective. Moreover, given the highly irregular puckered state in the final stretch laminates, it is virtually impossible to have attractive and sharply defined patterns of any kind printed onto them.

From a process standpoint, the more elastic strands or tapes are used, the more elasticity can be imparted to the stretch laminate and/or the more finely the strands or tapes can be distributed; but the more costly the laminate and the more complex the process becomes with a greater risk of strand or tape failure during construction and the issues of process reliability that result from it. There is a clear tradeoff between a fine dispersion of lower diameter strands and the increase in the occurrence of strand failure. Also, depositing large amounts of adhesive is always a challenge. Finally, thermal bonding of the laminates onto itself where seaming is needed to construct the product is difficult at high speed due to the high melting temperature of the nonwovens, and possibility of strand breakage. Thermal bonding also results in creep of strands in stretched laminates, i.e. strands coming lose and retracting.

As an alternative to the kind of "live stretch" produced by strand-based laminates, elastic film-based laminates have also been disclosed and used in so-called "zero-strain" structures. Examples of those are disclosed in US Patent Publications 2007/0287348 and 2008/0045917. In these, nonwovens may be bonded onto an elastic film and the laminate is then subjected to an activation process that unlocks the constraints imposed by the nonwoven and frees up the ability of the film to stretch and recover. These produce laminates structures which are very appealing for the look and feel and are ideal when introduced as stretchable outercovers in disposable absorbent products. However, in order for them to be effective, one might have to include high basis weight and somewhat costly elastic films, or they might offer only a limited range of stretch. Even if the high level of strain is achieved via use of higher film basis weight, the activated laminates do not look aesthetically appealing because of very defined corn-row like appearance, and somewhat broken nonwoven.

In view of all these issues, it is of great interest to create a different technology that can impart the high levels of stretch performance obtained in strands-based laminates, along with the process reliability and attractive final attributes of elastic film-based ones.

SUMMARY OF THE INVENTION

In one embodiment, the present invention relates generally to an absorbent article comprising a topsheet, an outer cover, and an absorbent core disposed between the topsheet and the outer cover, wherein the outer cover comprises a multilayer substrate. The multilayer substrate comprises a first outer layer and a second outer layer, wherein at least one of the first or second outerlayer comprises a component that exhibits at least partial elastic recovery after mechanical activation in the machine direction, and an inner layer, disposed between the first outer layer and the second outer layer, wherein the inner layer comprises elastic strands.

BRIEF DESCRIPTION OF THE DRAWINGS

The above-mentioned and other features and advantages of the present disclosure, and the manner of attaining them, will become more apparent and the disclosure itself will be better understood by reference to the following description of non-limiting embodiments of the disclosure taken in conjunction with the accompanying drawings, wherein:

FIGS. 6A-6C are schematics of inner and outer layers of one embodiment of the present invention.

FIGS. 8A-8C are schematics of inner and outer layers of one embodiment of the present invention.

DETAILED DESCRIPTION OF THE INVENTION

Figure 1:
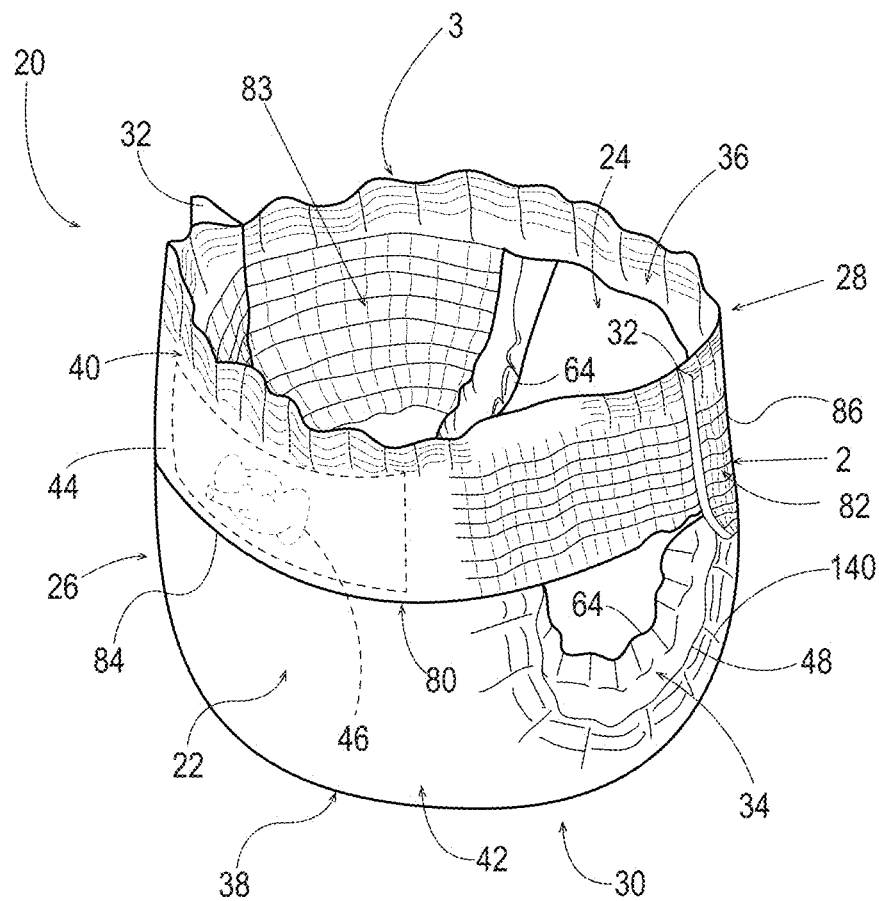
FIG. 1 is a perspective view of an exemplary disposable pull-on garment in a typical in-use configuration.

Various non-limiting embodiments of the present disclosure will now be described to provide an overall understanding of the principles of the structure, function, manufacture, and use of the apparatuses and methods disclosed herein. One or more examples of these non-limiting embodiments are illustrated in the accompanying drawings. Those of ordinary skill in the art will understand that the apparatuses and methods specifically described herein and illustrated in the accompanying drawings are non-limiting example embodiments and that the scope of the various non-limiting embodiments of the present disclosure are defined solely by the claims. The features illustrated or described in connection with one non-limiting embodiment may be combined with the features of other non-limiting embodiments. Such modifications and variations are intended to be included within the scope of the present disclosure.

Definitions:

In this description, the following terms have the following meanings:

The term "absorbent article" refers to a device that is placed against or in proximity to a body of a wearer to absorb and contain various exudates discharged from the body. Example absorbent articles comprise diapers, training pants, pull-on pant-type diapers (i.e., a diaper having a pre-formed waist opening and leg openings, such as illustrated in U.S. Pat. No. 6,120,487, issued to Ashton, on Sep. 19, 2000); belted pants (for example, U.S. Ser. Nos. 13/893,604, 13/764,990, 13/893,735, and 13/893,405), refastenable diapers, incontinence briefs and undergarments, diaper holders and liners, feminine hygiene garments, panty liners, and absorbent inserts, for example.

"Activatable nonwoven" refers specifically to nonwovens that have mechanical properties that interact well with films during the activation process. Activatable nonwovens of the present invention give tensile curves (ASTM D882-02, gauge length=5 mm, specimen width=25.4 mm, crosshead speed=2.117 mm/s, deformation direction coinciding with that applied during the activation process) characterized by relatively low maximum forces and relatively large engineering strains. Specifically, if the nonwoven's curve's maximum force point lies below 4 N/cm at an engineering strain value of greater than 100%, then, for the purposes of the present invention, it is deemed to be "activatable."

"Activated" refers to a material which has been mechanically deformed so as to impart elasticity to at least a portion of the material, such as, for example by incremental stretching. As used herein the term "activation" means any process by which tensile strain produced by intermeshing teeth and grooves causes intermediate web sections to stretch or extend. Such processes have been found useful in the production of many articles including breathable films, stretch composites, apertured materials and textured materials. For nonwoven webs, the stretching can cause fiber reorientation, change in fiber denier and/or cross section, a reduction in basis weight, and/or controlled fiber destruction in the intermediate web sections. For example, a common activation method is the process known in the art as ring rolling. U.S. Pat. Nos. 7,062,983, 6,843,134, 6,830,800, 5,143,679, and 5,167,897 disclose examples of the activation process.

"Adhesive" refers to compositions comprising one or more thermoplastic polymers, one or more tackifier resins, and typically a rheology modifier or plasticizer. Adhesives contain 2% or more of a tackifier resin. An adhesive is generally used to join or bond two or more materials together by applying it to at least one material and then bringing it into contact with at least one other material with sufficient force and for a sufficient duration of time, that the adhesive can wet out or spread on each material to join them together (see definition of "tackifier" below).

"Adhesive-free" refers to a laminate where an adhesive is not used to bond the elastomeric member (e.g., elastomeric film) to the nonwoven or nonwovens, and therefore an adhesive is not part of the final laminate structure.

"Adhesively bonded" or "adhesively laminated" refers to a laminate wherein an adhesive is used to bond an elastomeric member (e.g., elastomeric film) to a nonwoven(s) or to a second elastomeric member.

"Bicomponent fiber" refers to fibers or filaments consisting of material of two different compositions arranged across the cross-section of the fiber or filament. Each composition is typically delivered by a separate extruder to a spin pack designed to arrange the compositions into arrangements such as sheath-core, side-by-side, segmented pie and islands-in-the-sea. The mutual arrangement of different compositions can be beneficial in tailoring the chemical affinity between a film and a nonwoven in a laminate.

"Bilaminate" refers to multilayer composite comprising a film (monolayer or multilayer) and one nonwoven, which is formed by extrusion lamination, adhesive lamination, sonic welding or pressure bonding.

"Blocking" refers to the phenomenon of a film sticking to itself or to the opposite outer facing side of a composite laminate structure when the film or laminate is rolled, folded, or otherwise placed in intimate surface to surface contact.

"Body-facing," "inner-facing," "outer-facing," and "garment-facing" refer respectively to the relative location of an element or a surface of an element or group of elements. "Body-facing" and "inner-facing" imply the element or surface is nearer to the wearer's body during wear (i.e., closer to the wearer's body than a garment-facing surface or an outer-facing surface). "Garment-facing" and "outer-facing" imply the element or surface is more remote from the wearer during wear (i.e., element or surface is nearer to the wearer's garments that can be worn over the disposable absorbent article).

"Breathable" or "breathability" in reference to absorbent articles means that the absorbent article comprises a vapor-permeable layer or vapor-permeable multilayered structure that allows water vapor to pass out of the interior of the diaper. The Water Vapor Transmission Rate (WVTR, reported in $gm/m^2/day$), is a measure of breathability. WVTR is measured by the INDA/EDANA Worldwide Strategic Partners WSP 70.4 (08) standard test method.

"Comprise," "comprising," and "comprises" are open ended terms, each specifies the presence of what follows, e.g., a component, but does not preclude the presence of other features, e.g., elements, steps, components known in the art, or disclosed herein.

"Consisting essentially of" is used herein to limit the scope of subject matter, such as that in a claim, to the specified materials or steps and those that do not materially affect the basic and novel characteristics of the subject matter.

"Crystallization rate" refers to the kinetics of crystal nucleation and growth from a polymer melt, as it is cooled in, and following, an extrusion lamination process. Crystallization rate reflects the route by which a polymer solidifies from a molten, amorphous state. Differential Scanning calorimetry (DSC) may be used according to ASTM D 3418 as described in more detail in the Test Methods to determine crystallization rates of polymers, polymer blends, and formulations comprising polymers useful in films, including skin and tie layers, of the present invention.

As used herein "depth of engagement" (DOE) means the extent to which intermeshing teeth and grooves of opposing activation members extend into one another.

"Diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

"Disposable" in reference to absorbent articles, means that the absorbent articles are generally not intended to be laundered or otherwise restored or reused as absorbent articles (i.e., they are intended to be discarded after a single use and may be recycled, composted or otherwise discarded in an environmentally compatible manner).

"Disposed" refers to an element being positioned in a particular place with regard to another element. When one group of fibers is disposed on a second group of fibers, the first and second groups of fibers generally form a layered, laminate structure in which at least some fibers from the first and second groups are in contact with each other. In some embodiments, individual fibers from the first and/or second group at the interface between the two groups can be dispersed among the fibers of the adjacent group, thereby forming an at least partially intermingled, entangled fibrous region between the two groups. When a polymeric layer (for example a film), is disposed on a surface (for example a group or layer of fibers), the polymeric layer can be laminated to or printed on the surface.

As used herein, the terms "elastic," "elastomer," and "elastomeric" refer to any material which when evaluated using hysteresis method described below, extend to an engineering strain of at least 50% without breaking or rupturing, and is able to recover substantially to its original dimensions after the deforming force has been removed, i.e. show % set less than 30% according to hysteresis method described herein.

"Engineering strain" is the change in length of a specimen (in the direction of applied stress or strain) divided by the specimen's original length (William D. Callister Jr., "Materials Science and Engineering: An Introduction", 1985, John Wiley & Sons, Inc. New York, Chichester, Brisbane, Toronto, Singapore). To calculate percent engineering strain, the engineering strain is multiplied by 100.

"Ethylene rich" refers to the composition of a polymeric layer (e.g., a sheath of a bicomponent fiber or a skin layer of a film) or a portion of a layer of an EBL or nonwoven that comprises at least about 80% by weight of polyethylene (including homopolymers and co-polymers). For example, a sheath of a core-sheath bicomponent fiber, wherein the sheath is comprised of greater than about 80% by weight of a linear, low density polyethylene, is ethylene rich.

"Extensible", "plastic" and "extendibility" (e.g. extensible nonwoven, plastic film or extendibility of the elastomer), means the ability of material to stretch or elongate, without rupture or breakage, to at least 130% strain, for example, as described below in the Tensile Test "Extrusion bonded laminate ('EBL')" refers to a multilayer composite formed by extruding an elastomeric extrudate directly onto at least one nonwoven at or near a nip formed between two calender rollers, such that at least some nonwoven fibers penetrate into the soft extrudate film in order to join the film and the nonwoven. The amount of penetration of nonwoven into the soft extrudate may be controlled by selecting a nip gap smaller than the caliper of the nonwoven plus the film, by adjusting the pressure of the rolls, or by other means well understood to one of ordinary skill in the art. In one embodiment, the elastomeric extrudate may be a monolayer film comprising one or more elastomeric polymers. In another embodiment, the elastomeric extrudate may be a coextruded multilayer film with one or more outer layers and one or more inner layers.

"Extrusion lamination" or "extrusion coating" refers to processes by which a film of molten polymer is extruded onto a solid substrate (e.g., a nonwoven), in order to coat the substrate with the molten polymer film to bond the substrate and film together.

"Joined" refers to configurations whereby an element is directly secured to another element by affixing the element directly to the other element and to configurations whereby an element is indirectly secured to another element by affixing the element to intermediate member(s) which in turn are affixed to the other element. Materials may be joined by one or more bonding processes including adhesive bonding, thermal welding, solvent welding, ultrasonic bonding, extrusion bonding, and combinations thereof.

"Laminate" means two or more materials that are bonded to one another by methods known in the art, e.g., adhesive bonding, thermal bonding, ultrasonic bonding.

"Liquid-permeable" (or "liquid-pervious") and "liquid-impermeable" (or "liquid-impervious") refer to the penetrability of materials in the context of the intended usage of disposable absorbent articles. Specifically, "liquid permeable" refers to a layer or a layered structure having pores, openings, and/or interconnected void spaces that permit liquid water to pass through its thickness at less than 5 mbar of hydrostatic head (as defined by IVDA 80.6-01). Conversely, "liquid impermeable" refers to a layer or a layered structure through the thickness of which liquid water cannot pass through its thickness at less than 5 mbar of hydrostatic head (as defined by IVDA 80.6-01). A layer or a layered structure that is water-impermeable according to this definition may be vapor-permeable, for example permitting transmission of air and water vapor. Such a vapor-permeable layer or layered structure is commonly known in the art as "breathable."

"Machine direction" (also "MD" or "length direction") as applied to a film or nonwoven material, refers to the direction that was parallel to the direction of travel of the film or nonwoven as it was processed in the forming apparatus. The "cross machine direction" (also "CD" or "width direction") refers to the direction perpendicular to the machine direction.

"Outer cover" refers to that portion of the diaper which is disposed adjacent to the garment-facing surface of the absorbent core. Outer covers have tensile properties that enable ease of the application of the article, as well as enabling the article to conform to the wearer's body. In some embodiments it may prevent the excreta and/or exudates contained therein from soiling garments or other articles which may contact the diaper, such as bedsheets and clothing. In these embodiments, the outer cover may be impervious to liquids. In other embodiments, the outer cover may be liquid pervious. Outer covers of the present invention may be breathable. Outer covers of the present invention may comprise a multilayer laminate structure, including an EBL.

"Partial Elastic Recovery" refers to amount of recovery material exhibits upon removal of deforming force as described in the hysteresis method herein. For example, material is extend to an engineering strain of 50% as described in the hysteresis method, and shows 20% Set after the deforming force has been removed, i.e. it shows 80% partial elastic recovery according to hysteresis method described herein.

"Pant," "training pant," "pre-closed diaper," "pre-fastened diaper," "pull-on diaper," and "pant-like garment" as used herein, refer to disposable garments having a waist opening and leg openings designed for infant, children, or adult wearers. A pant can be configured such that the pant has a closed waist and leg openings prior to being donned on the wearer, or the pant can be configured such that the waist is closed and the leg openings formed while being donned on the wearer. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened, rear waist fastened). Examples of suitable pants are disclosed in U.S. Pat. Nos. 5,246,433; 5,569,234; 6,120,487; 6,120,489; 4,940,464; 5,092,861; 5,897,545; 5,957,908; and U.S. Patent Publication No. 2003/0233082 A1.

"Permanent set" is the permanent deformation of a material after removal of an applied load. Permanent set is typically expressed as a percent increase relative to the original size. It is measured as % Set as described in the Hysteresis Test.

"Petrochemical" refers to an organic compound derived from petroleum, natural gas, or coal.

"Petroleum" refers to crude oil and its components of paraffinic, cycloparaffinic, and aromatic hydrocarbons. Crude oil may be obtained from tar sands, bitumen fields, and oil shale.

"Plastoelastic" and "elastoplastic" as used herein are synonymous and refer to any material that has the ability to stretch in a substantially plastic manner during an initial strain cycle such as the one described in the hysteresis method below (i.e., applying a tensile force to induce strain in the material, then removing the force allowing the material to relax), yet which exhibits substantially elastic behavior and recovery during subsequent strain cycles, i.e when relaxed material is subjected to another strain cycle as per the hysteresis method below. Plastoelastic materials contain at least one plastic component and at least one elastic component, which components can be in the form of polymeric fibers, polymeric layers, and/or polymeric mixtures (including, for example, bi-component fibers and polymeric blends including the plastic and elastic components). Suitable plastoelastic materials and properties are described in U.S. 2005/0215963 and U.S. 2005/0215964.

"Propylene rich" refers to the composition of a polymeric layer (e.g., a sheath of a bicomponent fiber or a skin layer of a film) or a portion of a layer of an EBL or nonwoven that comprises at least about 80% by weight of polypropylene (including homopolymers and copolymers). For example, a tie layer comprising 96% VISTAMAXX 6102 (16% by weight PE/84% by weight PP), is propylene rich.

"Side panel," "front ear," "back ear," or "ear panel" refers to that portion of an absorbent article which is disposed adjacent to the outer cover or core or topsheet and connect a front waist edge to a back waist edge. Side panels or front/back ears have tensile properties that enable ease of the application of the article, as well as enabling the article to conform to the wearer's body. Side panels or front/back ears of the present invention may comprise a multilayer laminate, including an EBL. Examples of side panels that may be used in the present invention are described and illustrated in EP 1150833 (referenced as ear panels).

"Skin layer" refers to an outer layer of a coextruded, multilayer film that acts as an outer surface of the film during its production and subsequent processing.

"Substrate" as used herein describes a material that is primarily two-dimensional (i.e., in an XY plane) and whose thickness (in a Z direction) is relatively small (i.e. $\frac{1}{10}$ or less) in comparison to its length (in an X direction) and width (in a Y direction). Non-limiting examples of substrates include a web, layer or layers or fibrous materials, nonwovens, and films and foils, such as polymeric films or metallic foils, for example. These materials may be used alone or may comprise two or more layers laminated together. As such, a web is a substrate.

"Synthetic polymer" refers to a polymer which is produced from at least one monomer by a chemical process. A synthetic polymer is not produced directly by a living organism.

"Tackifier" refers to an adhesive component with a glass transition temperature in the range from about 70° C. to about 150° C. that decreases the melt viscosity of a rubbery polymer and increases the rubbery polymer's glass transition temperature and decreases the rubbery polymer's entanglement density.

"Tie layer" refers to a layer of a coextruded, multilayer film that acts as an intermediary between an inner layer of the film and another material, such that the laminate strength between the inner layer and the other material is improved (increased or decreased). The tie layer's composition can be adjusted to modify or optimize the chemical and physical interactions between film and nonwoven. Tie layers of the present invention do not contain more than 2% of a tackifier resin, and are substantially continuous over the entire surface of the coextruded film. In the present invention, it may be desirable to have a tie layer and skin layer which are compositionally identical.

"Web" means a material capable of being wound into a roll. Webs may be films, nonwovens, laminates, apertured laminates, etc. The face of a web refers to one of its two dimensional surfaces, as opposed to its edge.

"X-Y plane" means the plane defined by the MD and CD of a moving web or the length.

In one embodiment, it is an object of the invention to provide a uniaxially stretchable multilayer fabric or substrate consisting of a collection of prestrained elastic strands or tapes of elastic film positioned in between two outer layer structures. These outer layers encompass at least one prestrained elastic laminate structure made of a combination of stretchable nonwovens and/or film/nonwoven laminate structures that are mounted onto the prestrained elastic strands while the outer layer is in a stretched state. The outer prestrained layers are such that at least one of them includes a component material providing at least partial elastic recovery after mechanical activation in the machine direction (MD), namely in the same direction as the strands.

In some embodiments, it is further an object to create a uniaxially stretchable multilayer fabric or substrate with a reduced amount of gathering in at least one of the outer layers when such an outer layer is prestrained prior to bonding. The amount of gathering is controlled by the amount of prestrain applied onto at least one partially recoverable outer layer relative to that of the prestrained strands. It replaces regions having the puckered appearance of unstrained nonwovens with regions having the appearance and feel of an activated nonwoven. For instance, equal amount of prestraining in both the strands and the stretched outer layer will completely eliminate puckering, whereas applying an outer layer without any prestrain would exhibit similar puckering as seen in known nonwovens and products.

In other embodiments, an object of the invention is to allow for the reduction of the number or the size of strands by replacing a fraction of them with at least one stretchable and recoverable outer layer, the equivalence in mechanical performance dictating the balance between the actual number of strands being replaced and the stretch characteristics of a given outer elastic layer.

It is further object of the invention to provide a stretchable multilayer fabric or substrate with a means of tailoring its opacity and barrier properties.

It is a further object of the invention to use a laminate split into at least two components in the machine direction of the product to provide airflow through the multilayer structure.

It is a further object of the invention to reduce the amount of adhesive necessary to bond all the layers of the stretchable multilayer fabric or substrate together by reducing the amount of adhesive that penetrates the fiber assembly.

It is another object of the invention to provide elastomeric polyolefin-based strands that provide the option of discrete thermal bonding of the strands onto the outer layers.

It is another object of the invention to provide elastomeric styrene-based-copolymer-based strands with controlled rate of recovery.

It is another object of the invention to use thermal bonding capable of assembling both outer layers together with the elastic strands, further lowering the amount of adhesive needed as well as allowing the use of under-bonded webs in the construction of the outer layers. The combination of spunbond and meltblown layers with either one containing an elastomeric polymer is preferred to allow the use of under-bonded webs with higher extensibility during activation.

It is another object of the invention to create a stretchable multilayer fabric or substrate that can be thermally bonded more effectively via the incorporation of at least one lower melting elastomeric material in at least one of the outer layers. Of particular interest are stretch laminates that outperform current ones in their ability to form seams over the very short amounts of time experienced in sealing operations at high line speeds.

It is another object of the invention to provide more than one machine direction activation step to expand and fine-tune the range of stretch in either or both outer layers prior to or after the lamination process.

It is a further object of the invention to have at least one machine direction activation step on the stretchable multilayer fabric or substrate shortly after its assembly.

It is another object of the invention to have at least one machine direction activation step on the stretchable multilayer fabric or substrate prior to the one or several machine direction activation steps. The bonding patterns may be selected among a group capable of providing controlled apertures.

It is another object of the invention to provide a stretchable multilayer fabric or substrate that can expand in directions in addition to the machine direction with the use of multidirectional activation processes. These processes enable the local reorientation of the strands in part of the stretchable multilayer fabric or substrate as well as the dimensional growth of the fabric in directions other than the machine direction.

It is another object of the invention to provide a stretchable multilayer laminate with a gradient in stress profile and in the amount of gathering across its width.

It is another object of the invention to provide the use of the stretchable multilayered fabric or substrate in chassis components of a disposable absorbent product, whether as part of a stretchable outercover or of a belted structure.

It is a further object of the invention to provide a process for creating a stretchable multilayered fabric or substrate designed to improve visual and tactile appeal while lowering material usage.

It is an object of this invention to provide a process that enables the creation of a stretchable multilayered fabric or substrate with regions of different performance and appearance across the width and therefore capable of being used in different components of a belted stretchable chassis structure.

It is ultimately the object of the invention to provide a stretchable multilayer fabric or substrate that uses overall less material, whether in the strands content, in the basis weight of the outer layers, or the amount of adhesive needed.

Elastic Strands

Strands used in current "live stretch" laminates are typically made of polyester-polyurethane copolymer and are referred to by trade names such as Lycra. Other suitable examples include styrenic block copolymers and elastomeric polyolefins, in particular formulations rich in elastomeric polypropylene. In these materials, propylene represents the majority component of the polymeric backbone, and as a result, any residual crystallinity possesses the characteristics of polypropylene crystals. Residual crystalline entities embedded in the propylene-based elastomeric molecular network may function as physical crosslinks, providing polymeric chain anchoring capabilities that improve the mechanical properties of the elastic network, such as high recovery, low set and low force relaxation. Suitable examples of elastomeric polypropylenes include an elastic random poly(propylene/olefin) copolymer, an isotactic polypropylene containing stereoerrors, an isotactic/atactic polypropylene block copolymer, an isotactic polypropylene/random poly(propylene/olefin) copolymer block copolymer, a stereoblock elastomeric polypropylene, a syndiotactic polypropylene block poly(ethylene-co-propylene) block syndiotactic polypropylene triblock copolymer, an isotactic polypropylene block regioirregular polypropylene block isotactic polypropylene triblock copolymer, a polyethylene random (ethylene/olefin) copolymer block copolymer, a reactor blend polypropylene, a very low density polypropylene (or, equivalently, ultra low density polypropylene), a metallocene polypropylene, and combinations thereof. Suitable polypropylene polymers including crystalline isotactic blocks and amorphous atactic blocks are described, for example, in U.S. Pat. Nos. 6,559,262, 6,518,378, and 6,169,151. Suitable isotactic polypropylene with stereoerrors along the polymer chain are described in U.S. Pat. No. 6,555,643 and EP 1 256 594 A1. Suitable examples include elastomeric random copolymers (RCPs) including propylene with a low level comonomer (e.g., ethylene or a higher α-olefin) incorporated into the backbone. Suitable elastomeric RCP materials are available under the names Vistamaxx (available from ExxonMobil, Houston, Tex.) and VERSIFY (available from Dow Chemical, Midland, Mich.), and may include a fraction of a higher crystallinity polypropylene. An example of such a polypropylene is MFR 300. The ratio in some embodiments is about 90% to about 100% Vistamaxx, in others about 95% to about 100% Vistamaxx, and in still others about 97% to about 100%.

Bi-component strands are preferred to ensure anti-blocking with a low-crystallinity polyethylene-based formulation in the outerlayer that is called the sheath, coextruded with a very low-crystallinity elastomeric polypropylene that forms the core. Preferred low crystallinity polyethylene formulations include those described in US Patent Publication 2007/0287348, Autran, et al., assigned to P&G.

Some embodiments include strands made of a core made of about 90% to about 99% of an elastomeric polypropylene formulation that includes a majority of Vistamaxx and a sheath made of about 1% to about 9% of a polyethylene formulation. Other embodiments may have a core of about 92% to about 98% of an elastomeric polypropylene formulation and still other embodiments may have from about 95% to about 99%.

Other suitable commercially available polymers suitable for use as elastic strands include KRATON (styrenic block copolymer; available from the Shell Chemical Company, Houston, Tex.), SEPTON (styrenic block copolymer; available from Kuraray America, Inc., New York, N.Y.), VECTOR (styrenic block copolymer; available from Dexco Chemical Company, Houston, Tex.), ESTANE (polyurethane; available from Noveon, Inc., Cleveland, Ohio), PEBAX (polyether amide; available from Atofina Chemicals, Philadelphia, Pa.), and HYTREL (polyester; available from DuPont, Wilmington, Del.).

The elastic strands of the present invention may be prestrained prior to being assembled into laminates in order to maximize stretch/recovery.

For strand application, strand DTex (weight in gms per 10000 linear meter) can vary. Strand DTex ideal for application can be decided by amount of force the laminate needs to exert. Commonly available Spandex in the DTex range between 400 and 1900 can be employed to provide the right fit. Each Spandex strand comes wound on bobbin. The length of each spandex on bobbin is decided by the weight of the bobbin that process can handle. Bobbins are mounted on OETO (over end take off) or RTO.

| Strand Dtex (gms per 10000 linear meter) | Strand Diameter (mm) | Strand localized BW (gsm) |
| --- | --- | --- |
| 540 | 0.2404 | 224.7 |
| 680 | 0.2697 | 252.1 |
| 800 | 0.2925 | 273.5 |
| 1150 | 0.3508 | 327.9 |
| 1200 | 0.3583 | 334.9 |

| Strand Dtex (gms per 10000 linear meter) | Spacing between two strands (center to center) | Wt. Equivalent Elastic Film (gsm) |
| --- | --- | --- |
| 540 | 7 | 7.46 |
| 680 | 7 | 9.35 |
| 800 | 7 | 10.97 |
| 1150 | 7 | 15.64 |
| 1200 | 7 | 16.31 |

During the process of making a laminate, each individual strand is unwound from bobbin, and stretched to desired strain. The stretched strand is bonded to the nonwoven(s) or outer layers via adhesive, thermal bonding, ultrasonic bonding or any other bonding method available. For adhesive bonding process, the adhesive is either applied on strands or outer layer before combining. Ultrasonic or thermal bonding is carried out in a way that strand gets locked by selective bonding of outer layers. Bonded Strands as laminate go through activation process described below.

Outer Stretchable Elastic Layers

The outer layers that may surround the elastic strands on both sides may include two types:

1. Multilayer elastic nonwoven structures. These are layers that contain elastic fibers. These may be combined with plastic fibers in single or multiple layer structures. The size of a layer ranges from that typically produced in spunbond and meltblown processes, that is, from about 10 to about 40 microns for the former and from about 0.5 to about 5 microns for the latter. Spunbond fibers are preferred for their strength and durability, whereas opacity, toughness, and improved printability are imparted by incorporating one or several meltblown layers. These are preferably formulated to provide at least partial elasticity and contain at least about 25% elastomeric polypropylene, or at least about 50%, or at least about 75%. The plastic spunbond fibers have an average diameter in the range of about 10 to about 40 microns or from about 15 to about 35 microns, or from about 15 to about 30 microns, and are made of polyolefins with polypropylene- and polyethylene-based formulations found in a ratio from about 0 to about 100%. The fibers may be either mono- or bi-component fibers.

Examples of the elastic nonwoven structures include SSM, SSMS or SSMMS nonwovens, which describe various ways of combining spunbond (S) and meltblown (M)

layers. The outerlayer spunbond layers are preferably plastic-rich, meaning that the fibers represent the main components and are formulated to possess medium to high crystallinity polyolefins such as polyethylene or polypropylene. These are preferably formulated and constructed in a manner that favors their survivability during mechanical activation and are referred to as extensible or highly extensible spunbund nonwovens. Examples of such extensibles are found in prior granted U.S. Pat. Nos. 7,223,818, 7,776,771, and 8,182,456. Formulations may also include a fraction of an elastomeric polyolefin such as elastomeric polypropylene, and possibly a high MFR polypropylene component. Extensibility in MD is preferred in this invention.

The inner layer of the multilayer outer layer is preferably an elastic-rich combination of spunbond and meltblown layers. It is also possible to have one of several spunbond and meltblown layers made of a mixture of elastic and plastic fibers as disclosed in Patent Applications US2007287348, US2007287982, and US2007287983. At least one of the meltblown layers may be made of low diameter fibers prepared via a meltblown process and may contain at least one elastomeric polyolefin (VISTAMAXX from ExxonMobil, INFUSE from Dow, VERSIFY from Dow). The presence of several meltblown layers contributes to building up film-like properties and providing benefits such as opacity and barrier to adhesive among other features. The layer or layers with the smaller diameter fibers may also include so called nanofibers with sub-micron diameter.

The total basis weight of the elastic nonwoven structure is from about 30 gsm to about 120 gsm, or from about 30 to about 100 gsm, with the elastic fibers being from about 20 to about 70 gsm, and the plastic fibers from about 10 to about 50 gsm. Examples of multilayer fiber structures are disclosed in prior Patent Applications US2007287348, US2007287982, and US2007287983. The fiber assembly is mechanically activated to release its stretch/recovery features. Various set-ups may be used and provide different scenarios of accomplishing this objective. The benefits of having an elastomer-based meltblown layer are to ensure its survivability during mechanical activation and to avoid extensive shredding, but also to ease the bonding between all the layers by lowering the bonding temperature to significantly lower temperatures. This opens up the possibility of underbonding the spunbond fiber assembly, which induces less fiber damage at bond sites, which in turn is known to promote higher extensibility in both MD and CD during the activation process. The final laminate would preferably be subjected to more extensive thermal bonding further down the laminate assembly line to ensure complete integrity.

2. Film/nonwoven stretchable elastic bilaminate structures. These comprise various combinations of extruded elastic films with nonwovens. Again, the nonwovens are selected to exhibit highly extensibility in MD activation. Optionally the nonwovens may also include some elastic component as described before. However, the elasticity in designed to originate for the most part from the film itself. Examples of films and bilaminates have been described extensively in prior granted U.S. Pat. Nos. 8,445,744 and 8,168,853. In this invention thin elastic films are created with a variety of resins combined in at least one of several sublayers, the latter providing different benefits to the film.

The elastic film is preferably polyolefin-based, more preferably elastomeric polypropylene-based. The laminates are preferably low-cost extruded ones with little or no adhesive. One key feature in these bilaminates is for the film to have a skin layer to prevent blocking. The total basis weight of the laminate is from about 20 gsm to about 80 gsm, or from about 25 gsm to about 70 gsm, or from about 25 gsm to about 60 gsm, with the elastic film from about 10 gsm to about 40 gsm and the nonwoven from about 10 gsm to about 40 gsm. These have shown to be extensible in both MD and CD with about 60% to about 80% in the former and from about 120% to about 160% in the latter. There are several approaches to improve MD extensibility which are being disclosed. Because of tooth clearance issues on ring rolls, mechanical activation in MD is more limited to lower depths of engagement (DOE's). Process options that increase the range of MD extensibility beyond that provided by a single set of activation rolls are disclosed below. Underbonding the nonwoven may contribute to increasing the MD extensibility of the bi-laminate. Other means of increasing MD extensibility can be created by allowing either or both nonwoven fiber reorientation and/or nonwoven fiber deformation during the bi-laminate stretching process.

Stretchable Multilayer Fabric or Substrate

The stretchable multilayer fabric or substrate is created by assembling the inner layer comprising the elastic strands with at least one outer elastic layer. In one embodiment, the outer layer is only present on one side of the strand, the other side consisting of a non-elastic nonwoven. In another embodiment, both sides are made with elastic outer layers.

In one embodiment, at least one side is made of a film/nonwoven-based bilaminate. A small amount of adhesive in the range of from about 1 gsm to about 10 gsm, or from about 1 gsm to about 5 gsm, may be used to bond the strands to the outer layers, with only low levels needed when both stretchable outer layers are chosen to be film/nonwoven bilaminates. Thermal or Ultrasonic bonding may be used.

There are at least two processes for assembling the inner layer comprising strands with an outer layer in order to construct the final assembly. One way is to first subject the outer layer to an activation process in the machine direction. The outer layer may then be strained to some predetermined value prior to being brought in contact with the prestrained inner layer and bonded together (FIGS. 6A-6C). Another way is to first combine the outer layer and the inner layer together and then subject the assembly to activation in the machine direction (FIGS. 8A-8C). These two processes are discussed in more detail below.

As FIGS. 6A and 6B illustrate, in the first option, the process consists of subjecting each of the inner layer, 601 and the outer layer 602 to prestraining separately, FIG. 6A showing their length before stretching, and FIG. 6B depicting their length after stretching. The outer layer may be subjected to an activation process in the machine direction in order the release the stretch in that particular direction. There are two means of increasing the range of the available strains in this process while limiting the amount of damage produced in the nonwoven; (i) taking the outer layer through several successive activation units while maintaining some amount of prestrain between at least one contiguous set of units; or (ii) pre-activating the outer layer in the cross direction to pre-align the nonwoven fibers in the cross direction, hence providing more room for the fibers to subsequently orient in the machine direction. When several sets of rolls are used, it is also possible to heat up the web by contact against the first set of rolls, hence improving the deformability of the nonwoven webs.

The outer layer can be strained to some predetermined length, 603, and then brought in contact with the prestrained inner layer strands, 604, and adhesively bonded, resulting in the inner and outer layer assembly, 605, as shown in FIG.

6C. Preferred adhesive patterns are those that have the adhesive filaments oriented in the machine direction.

There are several scenarios for how much gathering, or puckering, ultimately results once the absorbent article is assembled, depending upon the relative values of the strain in the outer layer versus that of the inner layer. In FIG. 6B, the strain of the stretched outer layer 603 can be denoted as $\varepsilon_b$, and defined as $\varepsilon_b=(L_b-L_o)/L_o$, where $L_o$ is the original length of the outer layer, 601, and $L_b$ is the stretched length of the outer layer, 603. The strain of the stretched inner layer, 604, is denoted as $\varepsilon_s$, and defined by $\varepsilon_s=(L_s-L_o)/L_o$, where $L_o$ is the original length of the inner layer, 602, (same original length as for the outer layer), and $L_s$ is the stretched length of the inner layer, 604.

Figure 7A:
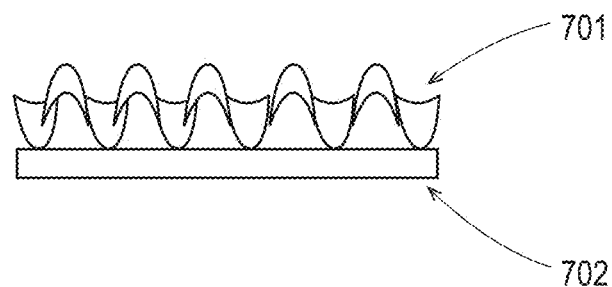
FIGS. 7A-7C are schematics of assemblies of inner and outer layers of embodiments of the present invention.
Figure 7B:
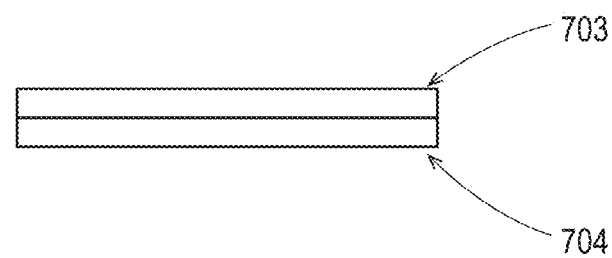
Figure 7C:
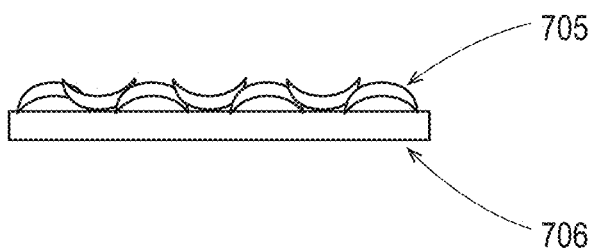

The spectrum of scenarios shown in FIGS. 7A-7C reflects the assembly in the relaxed state, with variations in the differential between the relative values of the strains, referred to as $(\varepsilon_s-\varepsilon_b)$. In the first case, FIG. 7A, the strain $\varepsilon_b$ of the outer layer, 701, is virtually equal to zero. The outer layer, 701, has no recovery, while the inner layer, 702, does, $\varepsilon_s$. This most closely resembles the type of construction obtained in the current assembly where nonwovens form the outer layer instead of the bilaminate used in this invention. Just as with a nonwoven outer layer, the outer layer has no recovery, and this results in a substantial amount of puckering that can be observed upon recovery of the complete assembly, as the outer layer gathers to comply with the retraction of the inner layer strands.

Puckering is the physical state used to describe the expansion of the assembly in the direction perpendicular to the plane. That is, a substrate may be defined as primarily two-dimensional, in the x-y plane. Similarly, any of the layers, such as an outer layer or an inner layer, or even the assembly of inner and outer layers, may still primarily be defined as two-dimensional, in the x-y plane. But when puckering occurs, that is, when one layer has greater strain than the strain of another layer to which it is bonded, the assembly may expand in the z-direction.

In the second scenario and at the opposite extreme, as depicted in FIG. 7B, $\varepsilon_b=\varepsilon_s$, thus $\varepsilon_s-\varepsilon_b=0$, and the outer layer, 703, undergoes complete recovery along with the inner layer, 704. In this instance no puckering can be expected. Moreover the outer layer fully contributes to the overall stretch performance profile. By doing so, it opens up the possibility of reducing the number of strands necessary to achieve the stretch requirements of a given product design.

A continuum of scenarios exist that correspond to intermediate values of $(\varepsilon_s-\varepsilon_b)$, which are depicted in FIG. 7C, where the outer layer, 705, has partial recovery, so when combined with the inner layer 706, some visible puckering occurs. The larger the differential the more puckering is observed. This is of great value as it offers a means of tailoring the aesthetics of the assembly and by extension that of the outer cover and this is of great value to the design of disposable absorbent products.

The second option for the process to assemble the inner and outer layers, as illustrated in FIGS. 8A-8C, consists in first taking the outer layer, 801, and the inner layer, 802, and creating the outer layer and inner layer assembly, 803, prior to subjecting the combined layers to activation in the machine direction, resulting in the stretched assembly, 804. As always, the process releases the stretch in that specific direction. The use of an adhesive is preferred to hold the outer layer onto the inner layer, with preferred adhesive patterns as those that have the adhesive layout of glue strings oriented in the machine direction.

As in the first processing option, in which the layers may be prestrained separately then joined, when the layers are first joined and then strained, there are two means of increasing the ultimate range of strains produced in the final assembly while limiting the amount of damage done to the nonwoven; (i) taking the outer layer through several activation units while maintaining some amount of prestrain between at least one set of contiguous units; or (ii) pre-activating the outer layer/inner layer assembly in the cross direction to pre-align the nonwoven fibers in the cross direction, hence providing more slacks for the fibers to subsequently orient in the machine direction. When several sets of rolls are used, it is also possible to heat up the web by contact against the first set of rolls, hence improving the deformability of the nonwoven webs.

The spectrum of constructions that are created that reflect the potential between the intrinsic type of recovery of the inner layer vs. that of the outer layer are the essentially the same for the second process as for the first. That is, FIG. 7A depicts the one extreme scenario, where $C_b$, the strain of the outer layer 801 when stretched, is nothing, $\varepsilon_b=0$, and there is maximum puckering, as the outer layer does not virtually recover at all. FIG. 7B depicts the other extreme scenario, where $\varepsilon_b=\varepsilon_s$, the outer layer strain roughly equals the inner layer strain, and no puckering occurs. The recovery of the outer layer matches that of the inner layer, and there is no expansion of the outer layer in the z-direction, perpendicular to the plane. FIG. 7C depicts a range of intermediate scenarios that fall between those depicted in 7A and 7B, with the outer layer having plastoelastic deformation profiles, where plasticity and elasticity are combined in response of the application of a strain: the more plasticity, the more puckering.

Another processing option simply combines both the first and second options discussed above, where part of the assembly construction is made with the prestrained outer layer, while the other is made via machine direction activation of the readily made one. Benefits may come from distributing the activations.

Tensile stress-strain curves can vary for the different construction scenarios, wherein the amount of puckering determines the point where the laminates start to contribute to the overall loading curve which adds up to that of the strands.

For both the first and second processing options, breathability may be an important attribute to the assembly. In the case where stretch elastic nonwoven form the outer layer, no special process is needed. In the scenario where a film is used, breathability may be achieved either by applying the well-known methods of dispersing calcium carbonate particles in the film formulation that create micro-pores upon stretching, or, alternatively, by ensuring that slits or holes are present within the final assembly. The slits may be either discrete or extend continuously along the machine direction.

Vacuum forming process can be used to make apertures in the film or outer layer. It is conceivable that a combination of stretch nonwoven and full elastic film or alternatively film strips may be constructed to form the outer layer.

Modes and Patterns of Mechanical Activation

The activation processes may be implemented through different scenarios. Variables may include the number of activation processes, their orders, and the locations by which they are applied onto the webs in order to release the right amount of stretch. The latter correlates with the depth of engagement (DOE) selected between interdigitated rolls. In all cases, the external layers are both activated in the machine direction (MD) to the maximum DOE possible using at least one set of activation rolls. Several sets of rolls may be mounted in series to release greater extensibility. The preferred execution is to arrange for a different relative positioning of the set of rolls so that the peaks and valleys of the interdigitated rolls match different segments of the web. In other words, web segments that were stretched between tooth locked unstretched segments are to be positioned to not stretch between the second set of rolls.

In a different scenario, the second set of rolls rotates at a higher speed than the first set of rolls, thus creating some MD strain on the web as it enters the second set of rolls. The amount of activation therefore compounds the first one, resulting in a greater amount of the overall activation.

Multilayer films, laminates, and substrates of the present invention may be mechanically activated by one or a combination of activating means, including, activating the web through intermeshing gears or plates, activating the web through incremental stretching, activating the web by ring rolling, activating the web by tenter frame stretching, and activating the web in the machine direction between nips or roll stacks operating at different speeds. Incremental stretching rollers may be used to activate multilayer films and laminates in the MD, CD, at an angle, or any combination thereof. In some embodiments, the depth of engagement used for incremental stretching is about 0.05 inches, about 0.10 inches, about 0.15 inches, about 0.20 inches, or about 0.25 inches. The depth of engagement can be, for example, at least about 0.05 inches or at least about 0.10 inches. The depth of engagement can be, for example, no more than about 0.10 inches, no more than about 0.18 inches, or no more than about 0.25 inches. The pitch of engagement can be, for example, from about 0.060 inches to about 0.200 inches, from about 0.080 inches to about 0.150 inches, or from about 0.100 inches to about 0.125 inches. Further, laminates may be activated at commercial rates via, for example, the ring rolling activation process. The activation may occur immediately after the lamination process or may occur as the laminate is unwound from a roll on which it was stored.

Absorbent Articles

Figure 2:
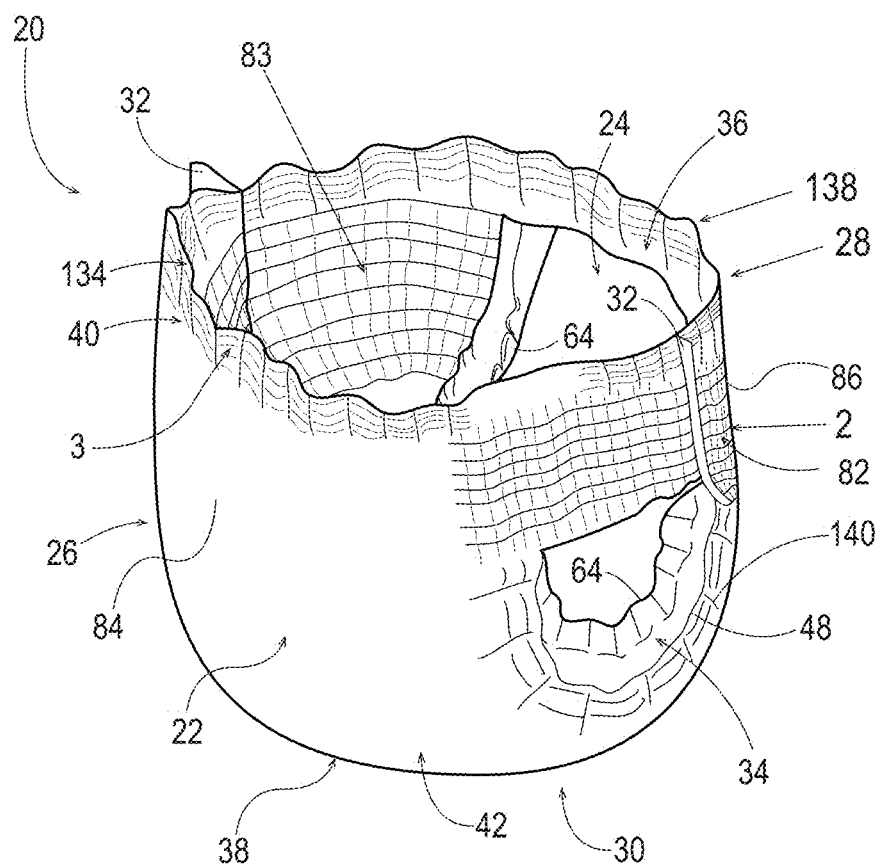
FIG. 2 is a perspective view of an exemplary disposable pull-on garment in a typical in-use configuration.

FIG. 1 is a perspective view of an absorbent article 20. FIG. 2 is a perspective view of an absorbent article 20. The absorbent article 20 has a longitudinal centerline L1 and a transverse centerline T1 (refer to FIG. 3 as well). The absorbent article 20 has an outer surface 22, an inner surface 24 opposed to the outer surface 22, a front region 26, a back region 28, a crotch region 30, and seams 32 which join the front region 26 and the back region 28 to form two leg openings 34 and a waist opening 36. Also referring to FIGS. 2 and 3, the absorbent article 20 comprises a main portion 1, a side portion 2, and a waist portion 3.

Figure 3:
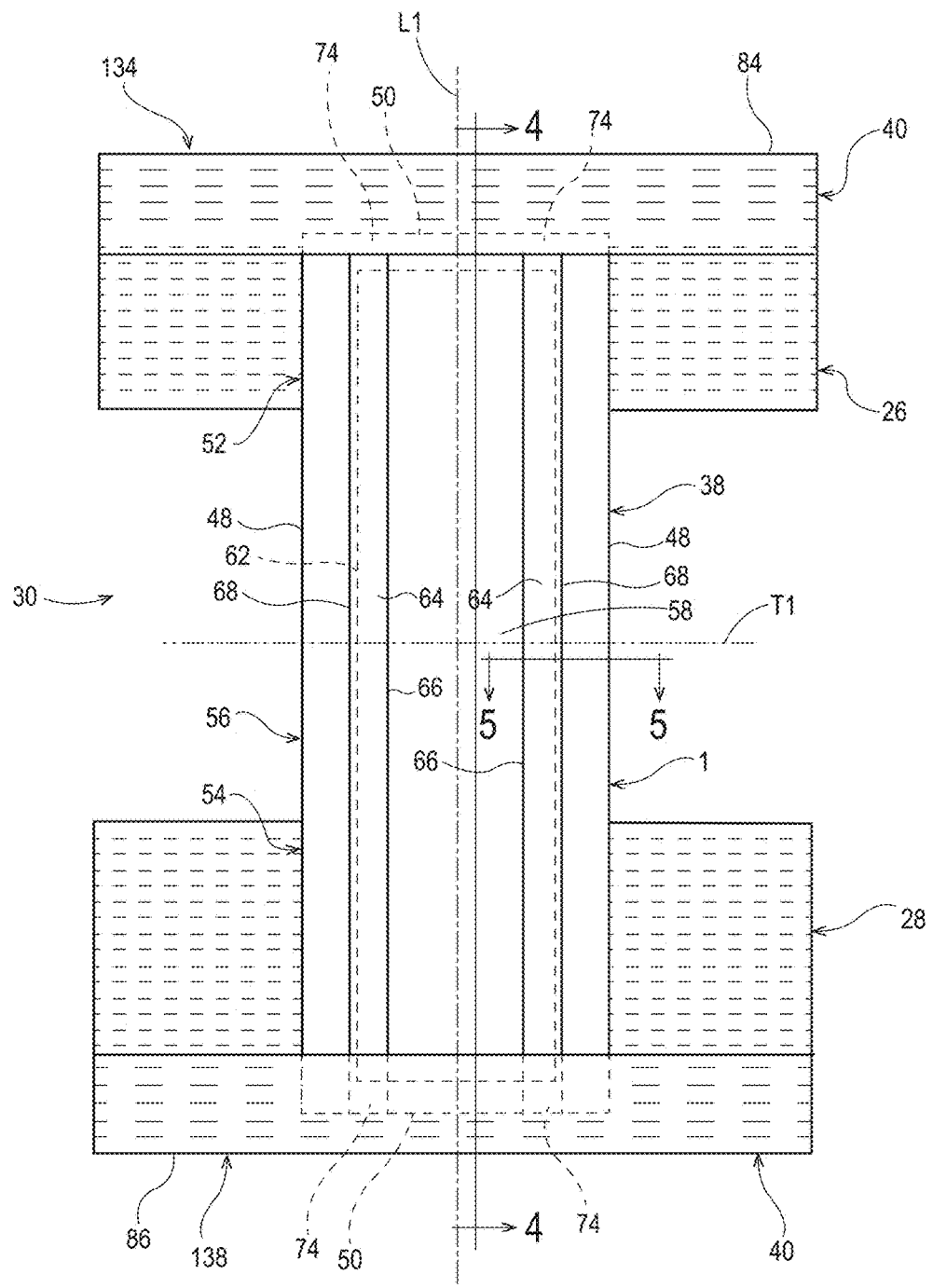
FIG. 3 is a plan view of the pull-on garment in its flat uncontracted condition showing the inner surface.

In the embodiment shown in FIGS. 1 and 3, the absorbent article 20 comprises an absorbent main body 38 (hereinafter may be referred to as "main body") to cover the crotch region of the wearer and a belt 40 extending transversely about the waist opening 36. The absorbent article 20 may also comprise an outer cover layer 42 to cover the main body 38. The belt 40 defines the waist opening 36. The belt 40, the main body 38 and/or the outer cover layer 42 jointly define the leg opening 34. The absorbent article 20 may have a patch sheet 44 printed with a graphic 46 thereon, which may be disposed in the front region 26 and/or the back region 28. Throughout, it is understood that the terms "outer cover" and "backsheet" may be used interchangeably.

The multi-layer substrates described herein may be used in an outer cover and/or may be used in a belt. That is, the materials described may be used in any outer layer of the articles described, whether referred to as an outer cover and/or a belt. It may also be considered, in some embodiments, that the outer cover includes the entire outer layer of the article, including a belt in some places in addition to non-belt places in others.

In the embodiment shown in FIG. 2 the absorbent article 20 comprises an absorbent main body 38 to cover the crotch region of the wearer and a belt 40 extending transversely about the waist opening 36. The absorbent article 20 may also comprise an outer cover layer 42 to cover the main body 38. The belt 40 defines the waist opening 36. The belt 40, the main body 38 and/or the outer cover layer 42 jointly define the leg opening 34. One or more of the belt layers may extend from a first waist edge 134 in a first waist region 26 through the crotch region to a longitudinally opposing second waist edge 138 in a second waist region 28 and forming a portion of the outer surface of the absorbent article 20.

The absorbent main body 38 absorbs and contains body exudates disposed on the main body 38. In the embodiment shown in FIG. 3, the main body 38 has a generally rectangular shape having a longitudinal centerline L1, a transverse centerline T1, left and right longitudinally extending side edges 48 (hereinafter may be referred to as "longitudinal side edge") and front and back transversely extending end edges 50 (hereinafter may be referred to as "transverse end edge"). The main body 38 also has waist panels (i.e., a front waist panel 52 positioned in the front waist region 26 of the absorbent article 20 and a back waist panel 54 positioned in the back waist region 28) and a crotch panel 56 in the crotch region 30 between the front and back waist panels 52, 54.

Figure 4A:
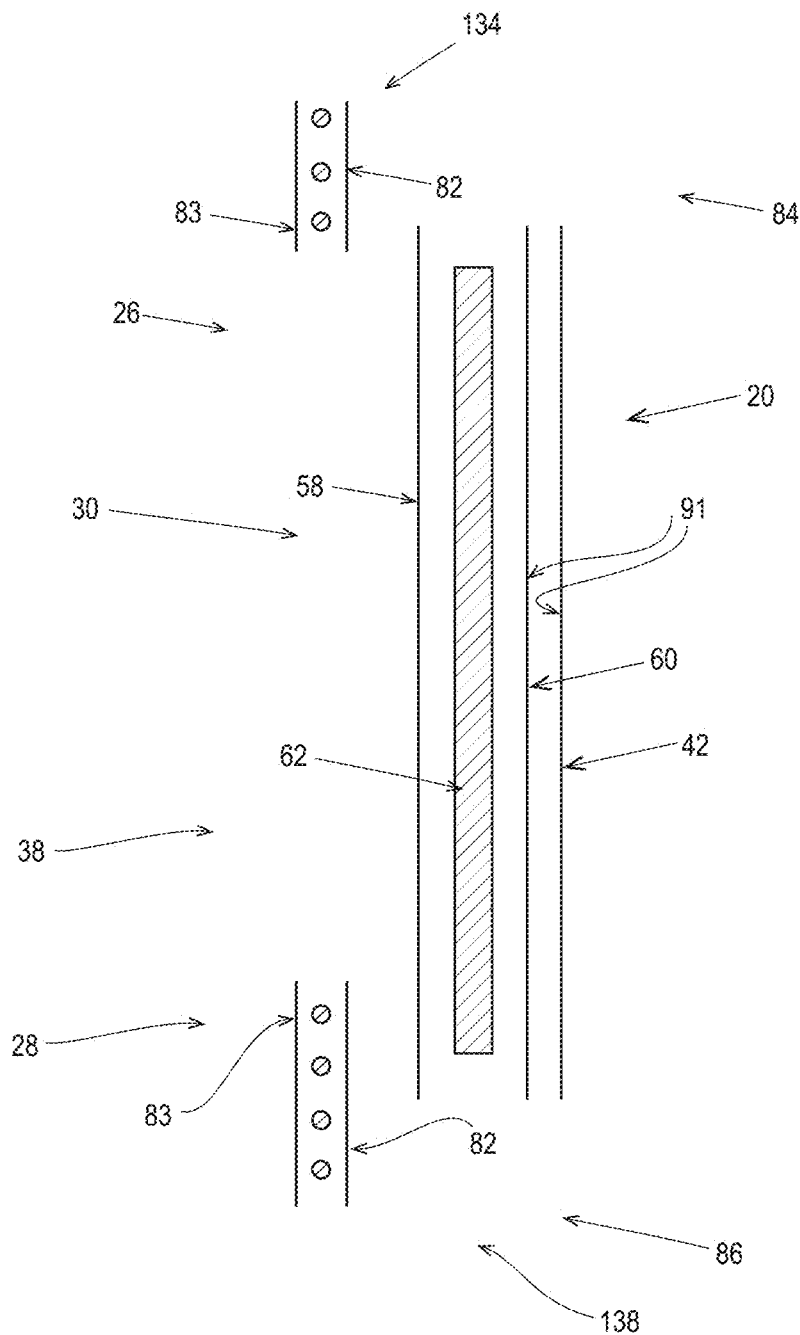
FIG. 4a is a schematic cross section view of a first embodiment taken along line 4-4 in FIG. 3 of an exemplary disposable pull-on garment.
Figure 4B:
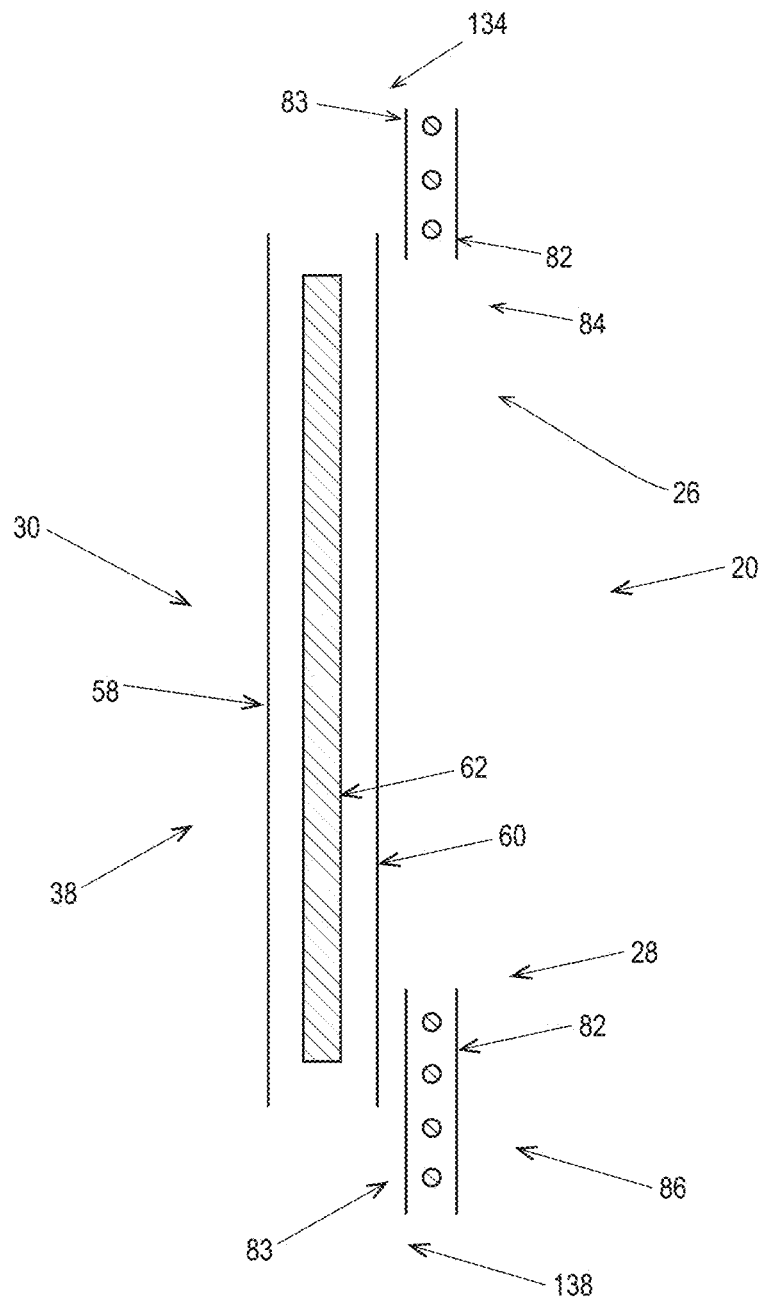
FIG. 4b is a schematic cross section view of a second embodiment taken along line 4-4 in FIG. 3 of an exemplary disposable pull-on garment.

In the embodiment shown in FIGS. 4a and 4b, the absorbent articles 20 may comprise front and rear belts 84, 86 intended to encircle at least a portion of the waist of the wearer, the front and rear belt portions 84, 86 being connected by a main body 38 forming the crotch region 30 of the absorbent article 20. The front and rear belts 84 and 86 may be formed from a first belt layer forming a portion of the outer surface 22 of the absorbent article, the first belt layer 82 may be formed of two longitudinally spaced webs of material. The front and rear belts 84 and 86 may also comprise a second belt layer 83 forming a portion of the inner surface 24 of the absorbent article 20, the second belt layer 83 may also be formed of two longitudinally spaced webs of material. The second belt layer may also be discontinuous and spaced apart in a transverse direction. The first and second belt layers 82, 83 may be formed of substantially the same material or may comprise different materials. The first and second belt layers 82, 83 may be formed from nonwovens, films, foams, elastic nonwoven, or combinations thereof. The front and rear belts 84, 86 may also comprise an elastomeric material disposed between the first and second belt layers 82, 83. The elastomeric material may comprise one or more elastic strands, elastomeric films, elastomeric ribbons, elastomeric nonwovens, elastomeric filaments, elastomeric adhesives, elastomeric foams, scrims or combinations thereof. A portion of the elastomeric material may be directly combined with the outer cover layer. The main body 38 of the absorbent article may comprise an outer surface 22, backsheet 60, an inner surface 24, topsheet 58, an absorbent core 62 disposed between the topsheet 58 and the backsheet 60, and an outer cover 42. The backsheet may be formed of a nonwoven material, woven material, films or laminates comprising a combination of one or more of these materials. In one embodiment the backsheet is a film and nonwoven laminate wherein the nonwoven of the laminate is the outer cover layer. In addition, the main body 38 may comprise elasticized barrier leg cuffs 64 disposed at or adjacent the side edges of the main body. The front and rear belts 84, 86 may overlap at least a portion of the main body and one or both of the belt portions may be disposed on the outer surface of the main body or alternatively on the inner surface of the main body. A portion of the second belt layer and/or a portion of the first belt layer may be directly attached to the outer cover layer. Alternatively, the front belt and rear belt 84, 86 may comprise longitudinally spaced webs of material forming a first surface of the belt wherein the webs are folded along the waist edge, or alternatively the leg opening edge, of the belt to wrap the elastomeric material and form at least a portion of the second surface of the belt. In other words, at least a portion of the inner surface and outer surface of each of the belt portions may be formed from a single web of material.

Figure 4C:
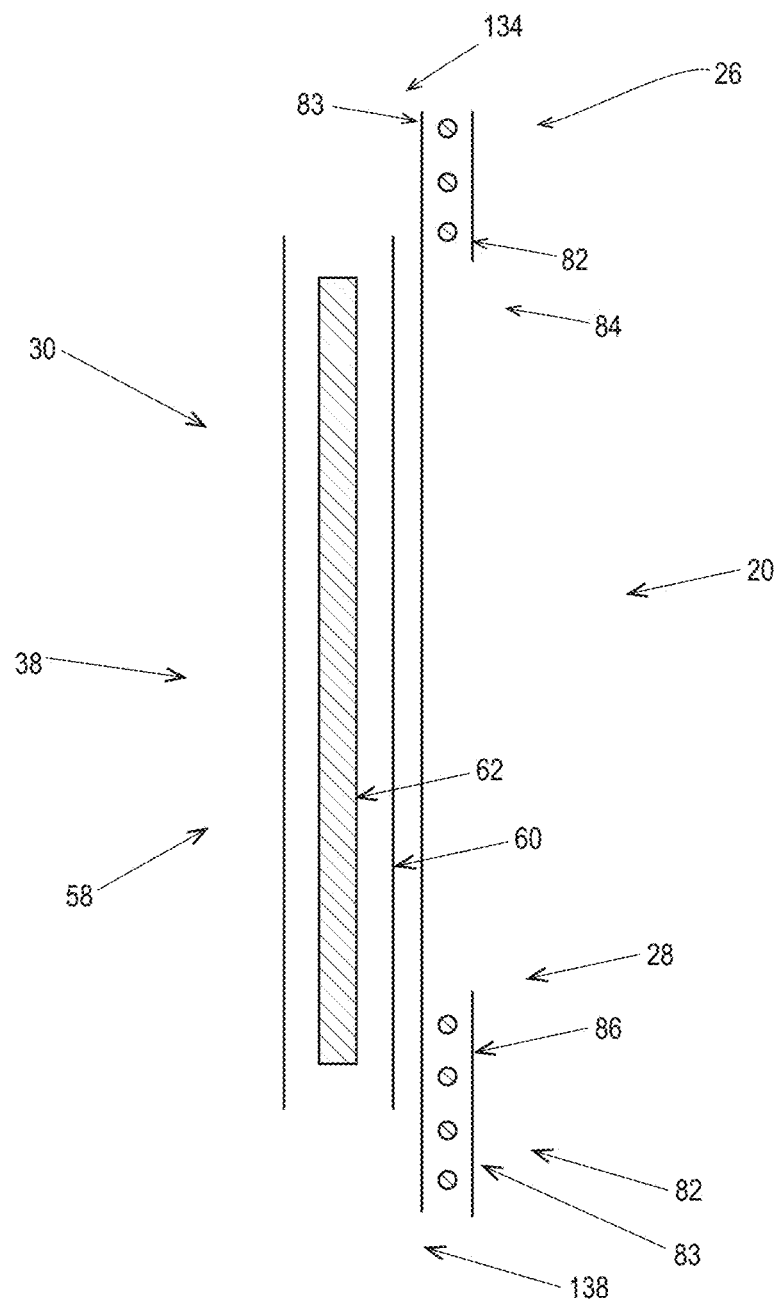
FIG. 4c is a schematic cross section view of a third embodiment taken along line 4-4 in FIG. 3 of an exemplary disposable pull-on garment.
Figure 4D:
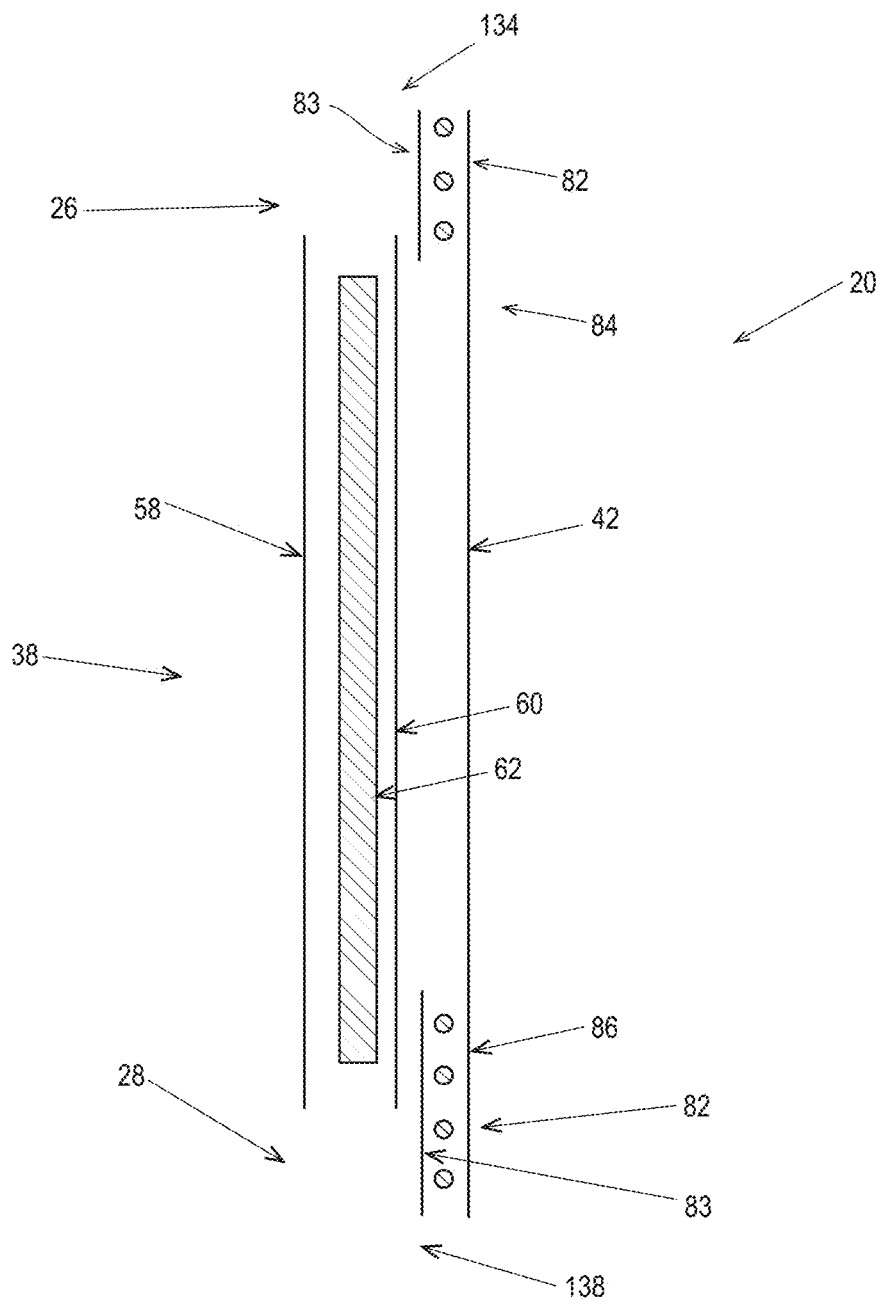
FIG. 4d is a schematic cross section view of a fourth embodiment taken along line 4-4 in FIG. 3 of an exemplary disposable pull-on garment.

In the embodiment shown in FIGS. 4c and 4d, the absorbent articles 20 may comprise front and rear extensible belts 84, 86 disposed in the front and rear waist regions 26, 28 respectively and intended to encircle at least a portion of the waist of the wearer, the front and rear belts 84, 86 being connected by the main body that forms the crotch region 30 of the article. The first and second belt may be formed from a first belt layer extending from a first waist edge 134 in a first waist region 26 through the crotch region to a longitudinally opposing second waist edge 138 in a second waist region 28 and forming a portion of the outer surface of the absorbent article 20. The front and rear belts 84, 86 also may comprise a second belt layer 83 forming a portion of the inner surface of the absorbent article, the second belt layer may be formed of two longitudinally spaced webs of material. The first and second belt portions may also comprise an elastomeric material disposed between the first and second belt layers. The elastomeric material may comprise elastic strands, elastomeric films, elastomeric ribbons, elastomeric nonwovens, elastomeric filaments, elastomeric adhesives, elastomeric foams, scrims or combinations thereof. The main body 38 of the absorbent article may comprise an outer surface 22, backsheet 60, an inner surface 24, topsheet 58, and an absorbent core 62 disposed between the topsheet 58 and the backsheet 60. The first belt layer may form a portion of the outer surface 22. In addition, the main body may comprise elasticized barrier leg cuffs 64 disposed at or adjacent the side edges of the main body. The second belt layer may overlap at least a portion of the main body and one or both of the second belt layer webs may form the outer surface of the first belt layer or alternatively the inner surface of the first belt layer. Alternatively, the front portion and/or the rear portion of the first belt layer may be folded along the waist edge of the belt region to wrap the elastomeric material and form a portion of the second belt layer of one or both of the front and rear belt portions 84, 86. In other words, the inner surface and outer surface of each of the belt portions is formed from a single web of material.

Figure 4E:
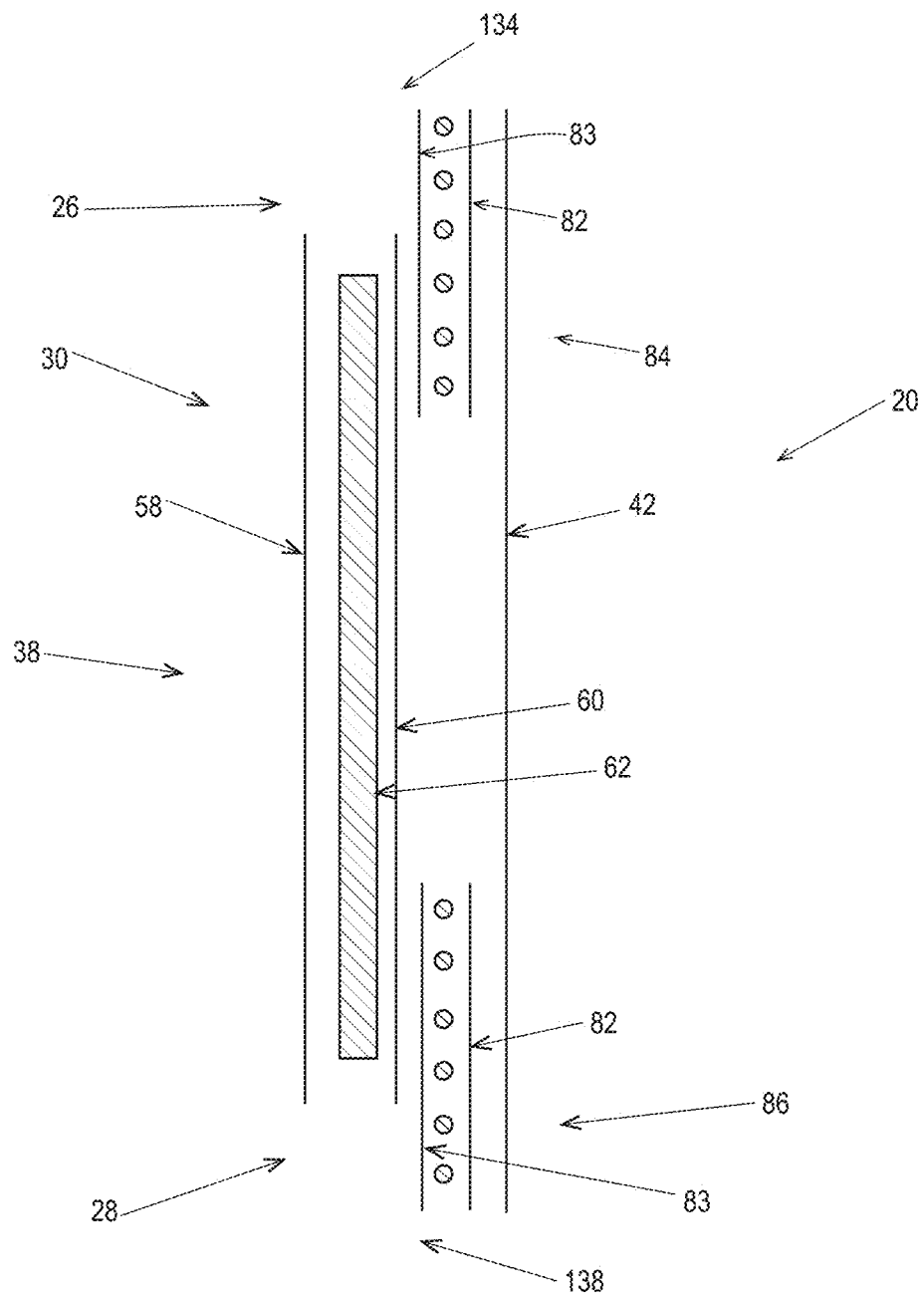
FIG. 4e is a schematic cross section view of a sixth embodiment taken along line 4-4 in FIG. 3 of an exemplary disposable pull-on garment.
Figure 4F:
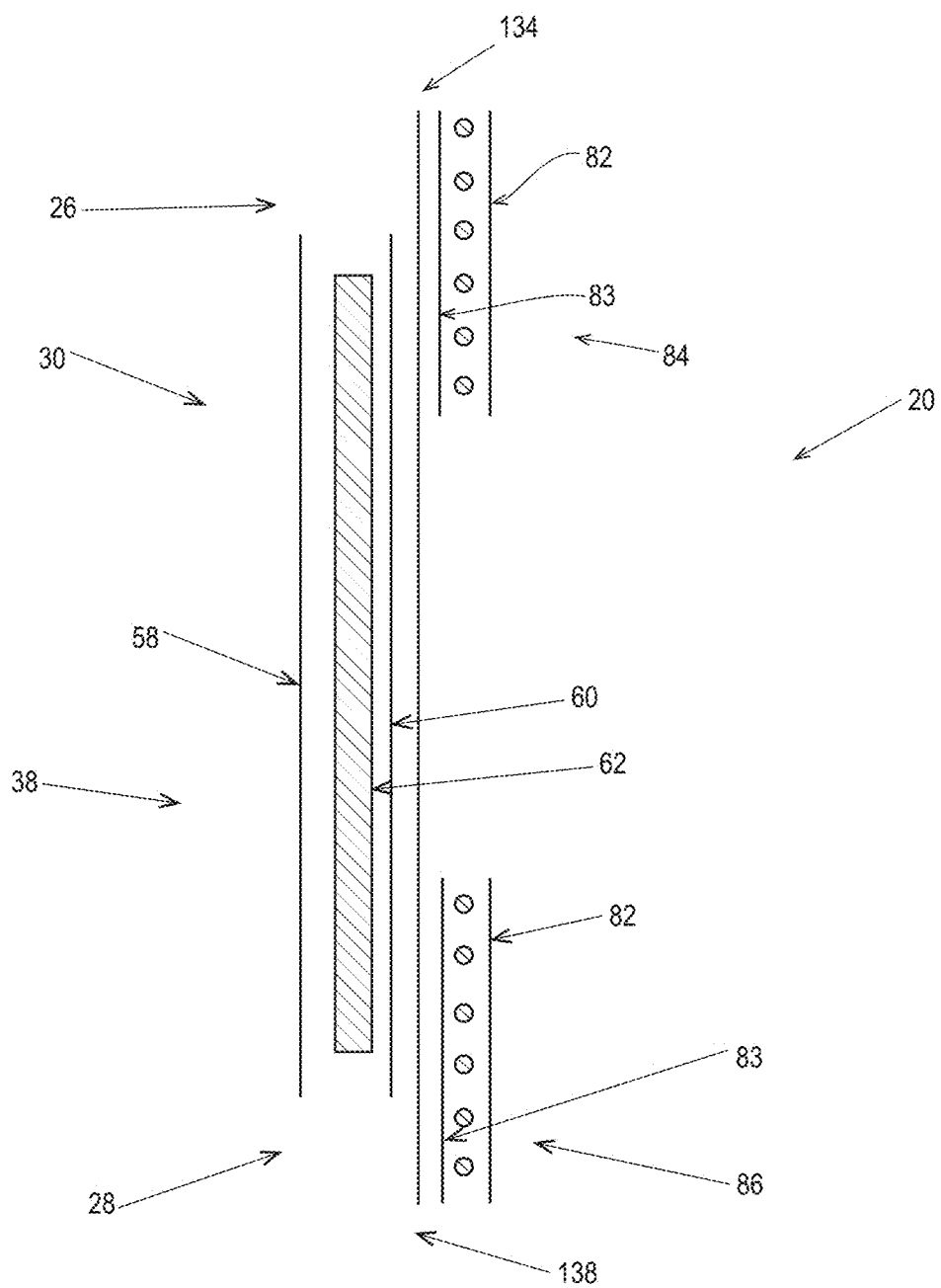
FIG. 4f is a schematic cross section view of a seventh embodiment taken along line 4-4 in FIG. 3 of an exemplary disposable pull-on garment.

In the embodiment shown in FIGS. 4e and 4f, the absorbent articles 20 may comprise a full outer cover layer 42, extending from a front waist edge 134 in a first waist region 26, through the crotch region to the longitudinally opposing rear waist edge 138 in a second waist region 28. The article may also comprise front and rear belts 84, 86 intended to encircle the waist of the wearer, the front and rear belts 84, 86 being connected to the outer cover layer 42 and/or the main body 38 of the absorbent article 20. The first and second belts are formed from a first belt layer forming a portion of the outer surface of the belt, the first belt layer being formed of two longitudinally spaced webs of material. The first and second belt portions also comprise a second belt layer forming a portion of the inner surface of the absorbent article, the second belt layer also being formed of two longitudinally spaced webs of material. The first and second belt layers may be formed of substantially the same material or may comprise different materials. The first and second belt layers may be formed from nonwovens, films, foams or combinations thereof. The first and second belts may also comprise an elastomeric material disposed between the first and second belt layers. The elastomeric material may comprise elastic strands, elastomeric films, elastomeric ribbons, elastomeric nonwovens, elastomeric filaments, elastomeric adhesives, elastomeric foams, scrims or combinations thereof. The first and second belts may be disposed on the interior surface of the outer cover layer. Alternatively, the first and second belts may be disposed on the outer surface of the outer cover layer. In such an embodiment the outer cover layer would for a portion of the inner surface of the article in the waist regions and the first belt layer would form a portion of the outer surface of the article. The second belt layer when present may be disposed between the first belt layer and the outer cover layer. The main body 38 of the absorbent article 20 may comprise an outer surface 22, backsheet 60, an inner surface 24, topsheet 58, and an absorbent core 62 disposed between the topsheet 58 and the backsheet 60. In addition, the main body 38 may comprise elasticized barrier leg cuffs 64 disposed at or adjacent the side edges of the main body 38. One or both of the front and rear belts 84, 86 may overlap at least a portion of the main body 38 and one or both of the belts may be disposed on the outer surface of the main body 38 or alternatively on the inner surface of the main body 38. One or both of the front and rear belts 84, 86 may be disposed on the interior surface of the outer cover layer or alternatively one or both of the belts may be disposed on the exterior surface of the outer cover layer. One or both of the front belt and rear belt 84, 86 may comprise longitudinally spaced webs of material forming a first surface of the belt wherein the webs are folded along the waist edge 36 of the belt to wrap the elastomeric material and form at least a portion of the second surface of the belt. In other words, a portion or the entirety of the inner surface and outer surface of one or both of the belt portions may be formed from a single web of material. The rugosities, wrinkles, folds in one or both of the front and rear belts may have a different configuration, size, orientation, shape, etc. than that of the outer cover layer.

Figure 4G:
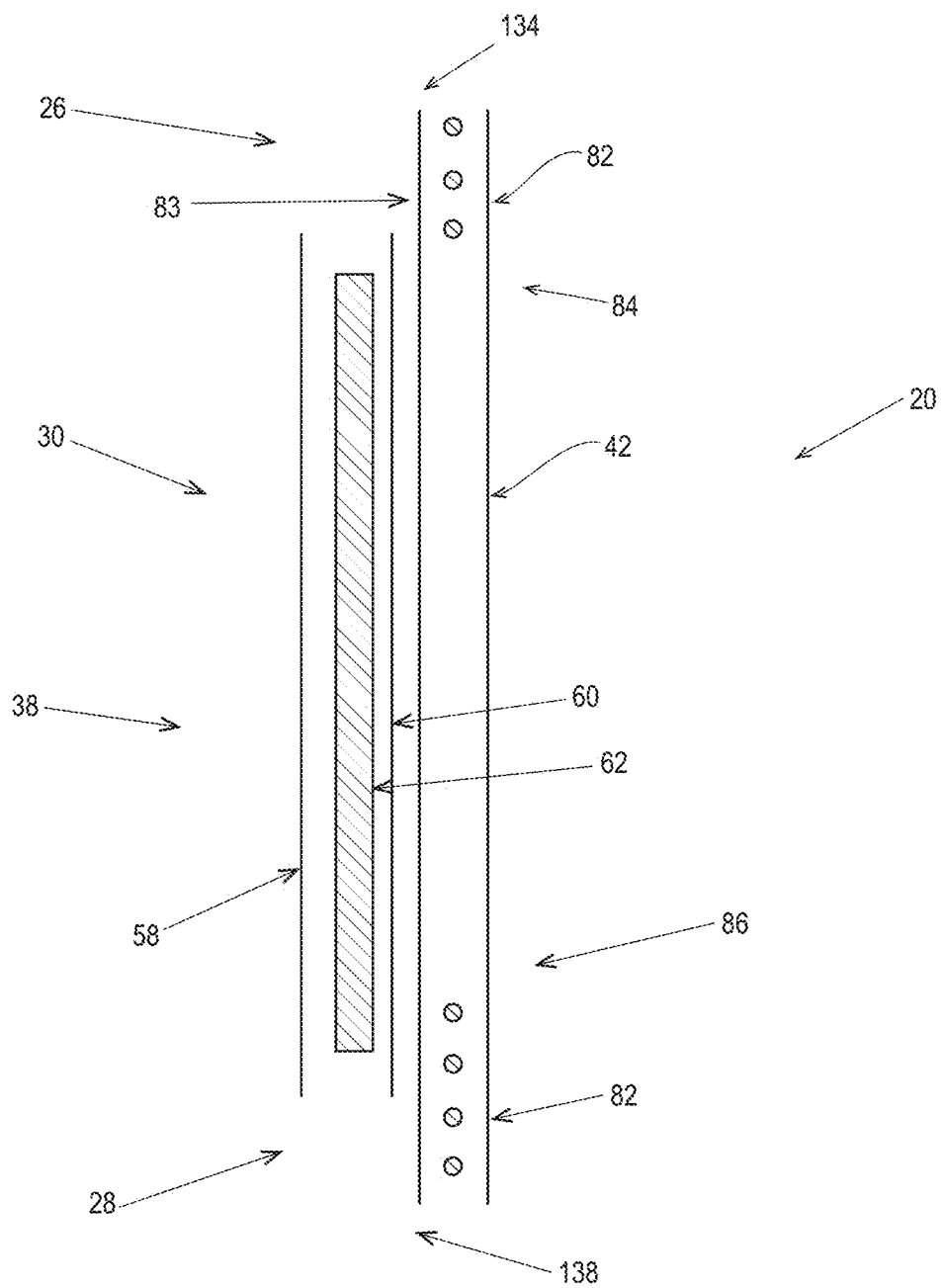
FIG. 4g is a schematic cross section view of an eight embodiment taken along line 4-4 in FIG. 3 of an exemplary disposable pull-on garment.

In the embodiment shown in FIG. 4g, the absorbent articles 20 may comprise front and rear belts 84, 86 intended to encircle at least a portion of the waist of the wearer, the front and rear belts 84, 86 being connected to a main body 38 forming a portion of the crotch region 30 of the absorbent article 20. The front and rear belts 84, 86 are formed from a first belt layer forming a portion of the outer surface of the absorbent article. The front and rear belt portions 84, 86 also comprise a second belt layer 83 forming a portion of the inner surface 24 of the absorbent article 20. The second belt layer may be laterally discontinuous and spaced apart in a transverse direction. The first and second belt layers 82, 83 may be formed of substantially the same material or may comprise different materials. The first and second belt layers 82, 83 may be formed from nonwovens, films, foams or combinations thereof. The front and rear belt portions 84, 86 may also comprise an elastomeric material disposed between the first and second belt layers 82, 83. The elastomeric material may comprise elastic strands, elastomeric films, elastomeric ribbons, elastomeric nonwovens, elastomeric filaments, elastomeric adhesives, elastomeric foams, scrims or combinations thereof. A portion of the elastomeric material may be directly combined with the outer cover layer. The main body 38 of the absorbent article may comprise an outer surface 22, backsheet 60, an inner surface 24, topsheet 58, and an absorbent core 62 disposed between the topsheet 58 and the backsheet 60. In certain embodiments the backsheet may be a nonwoven and film laminate wherein the nonwoven is formed by the outer cover layer. In addition, the main body 38 may comprise elasticized barrier leg cuffs 64 disposed at or adjacent the side edges of the main body 38. The front and rear belts 84, 86 overlap at least a portion of the main body 38 and one or both of the belts may be disposed on the outer surface of the main body 38 or alternatively on the inner surface of the main body 38. A portion of the second belt layer and/or a portion of the first belt layer may be directly attached to the outer cover layer. The front and rear belts 84, 86 may be formed from a first belt layer extending from a first waist edge 134 in a first waist region 26 through the crotch region to a second waist edge 138 in a second waist region 28 and forming a portion of the outer surface of the absorbent article 20. The front and rear belts 84, 86 may also comprise a second belt layer extending from a first waist edge 134 in a first waist region 26 through the crotch region to a second waist edge 138 in a second waist region 28 and forming a portion of the inner surface of the absorbent article 20. The first and second belt layers may be formed of substantially the same material or may comprise different materials. The first and second belt layers may be formed from nonwovens, films, foams, woven materials or combinations thereof. The front and rear belt portions 84, 86 may also comprise an elastomeric material disposed between the first and second belt layers in one or both of the first and second waist regions 26, 28. The elastomeric material may comprise elastic strands, elastomeric films, elastomeric ribbons, elastomeric nonwovens, elastomeric filaments, elastomeric adhesives, elastomeric foams, scrims or combinations thereof. The main body 38 of the absorbent article 20 may comprise an outer surface 22, backsheet 60, an inner surface 24, topsheet 58, and an absorbent core 62 disposed between the topsheet 58 and the backsheet 60. One or both of the first and second belt layers may form a portion of the outer surface 22. In addition, the main body 38 may comprise elasticized barrier leg cuffs 64 disposed at or adjacent the side edges of the main body 38. A portion of one or both of the front and rear belts 84, 86 may overlap at least a portion of the main body 38. Alternatively, the front belt portion and rear belts 84, 86 may comprise a belt layer forming a first surface of the belt portion wherein the belt layer may be folded along the waist edge of the belt portion to wrap the elastomeric material and overlap a portion of the opposing belt layer. In other words, a portion of the inner surface and a portion of the outer surface of each of the belt portions may be formed from a single web of material.

Figure 5:
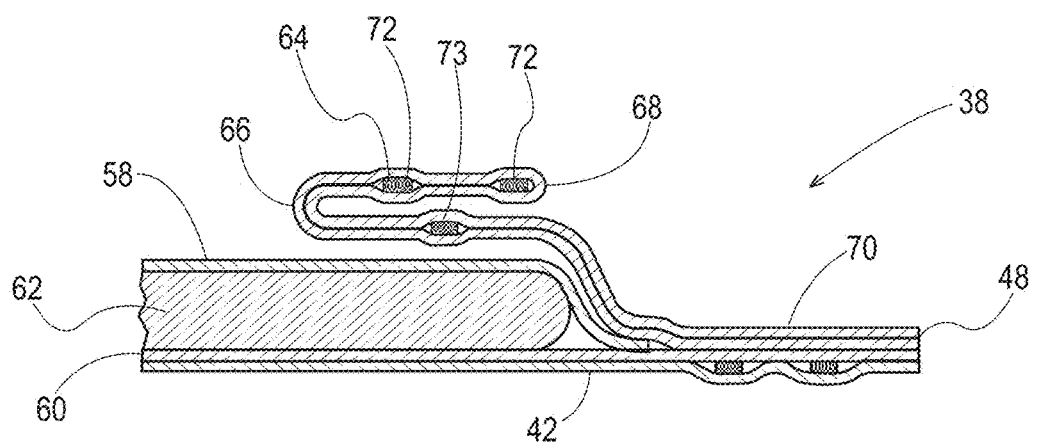
FIG. 5 is a schematic cross section view taken along line 5-5 in FIG. 3 of an example of a folded outer leg cuff suitable in one embodiment of the invention.

The main body 38 may comprise a liquid pervious topsheet 58, a liquid impervious backsheet 60 and an absorbent core 62 disposed therebetween. The main body 38 may additionally comprise a barrier leg cuff 64 disposed along the longitudinal side edge 48. The barrier leg cuff 64 provides improved containment of liquids and other body exudates in the crotch region 30. The barrier leg cuff 64 shown in FIG. 5 comprises a single layer of material which may be folded to form a barrier leg cuff having two layers. The barrier leg cuff 64 extends from the side of the main body at or adjacent the longitudinal side edge 48 toward the longitudinal centerline L1. The barrier leg cuff may be folded along the folding line 66 back toward the longitudinal side edge 48. The barrier leg cuff 64 may have a first barrier cuff elastic material 72 adjacent to the distal portion 68 and a second barrier cuff elastic material 73 adjacent to the proximal portion 70 of the barrier leg cuff 64. The proximal portion 70 of the barrier leg cuff 64 may be joined to the backsheet 60 adjacent to the longitudinal side edge 48. The portion of the barrier leg cuff 64 along the folding line 66 and the distal portion 68 may be free from attachment to any portion of the main body 38 in the crotch region 30 such that the barrier leg cuff 64 stands up toward the wearer's body. The transverse end 74 of the barrier leg cuff 64 may be joined to the topsheet 58 at or adjacent the longitudinally opposing ends of the leg cuff by an attachment means which may be any known means such as an adhesive, heat bond, pressure bond or the like as shown in 5.

The liquid pervious topsheet 58 may be positioned adjacent the body-facing surface of the absorbent core 62 and may be joined thereto and/or to the backsheet 60 by any attachment means known in the art. The liquid impervious backsheet 60 is generally that portion of the absorbent article 20 positioned adjacent the garment-facing surface of the absorbent core 62 and prevents the exudates absorbed and contained therein from soiling articles that may contact the absorbent article 20. The absorbent core is positioned between the topsheet 58 and the backsheet 60 and absorbs and retains liquids such as urine and other certain body exudates.

The topsheet 58, the backsheet 60 and the absorbent core may be manufactured any known materials. Suitable topsheet materials may include porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Suitable backsheet materials may include breathable materials that permit vapors to escape from the diaper while still preventing exudates from passing through the backsheet.

A suitable absorbent core for use in the absorbent article 20 may comprise any absorbent material which is generally compressible, conformable, non-irritating to the wearer's skin, and capable of absorbing and retaining liquids such as urine and other certain body exudates. In addition, the configuration and construction of the absorbent core may also be varied (e.g., the absorbent core(s) or other absorbent structure(s) may have varying caliper zones, hydrophilic gradient(s), a superabsorbent gradient(s), or lower average density and lower average basis weight acquisition zones; or may comprise one or more layers or structures). In some embodiments, the absorbent core may comprise a fluid acquisition component, a fluid distribution component, and a fluid storage component. An example of a suitable absorbent core having a fluid acquisition component, a fluid distribution component, and a fluid storage component is described in U.S. Pat. No. 6,590,136.

The outer cover layer 42 may be disposed on the outer surface 22 of the absorbent article 20 and covers the crotch panel 56 of the absorbent main body 38. The outer cover layer 42 may extend into and cover the front waist panel 52 and the back waist panel 54 of the main body 38. The outer cover layer may form a portion of the backsheet and/or the main body. The outer cover layer 42 may be directly joined to and cover a portion or all of the liquid impervious backsheet 60 of the main body 38. The central panel 80 of the front and back belt 84, 86 may be joined to the front waist panel 52 and the back waist panel 54 of the main body 38 through the outer cover layer 42. Thus, the outer cover layer 42 is disposed between the front and back belt 84, 86 and the liquid impervious backsheet 60 of the main body 38. In one embodiment shown in FIGS. 2 and 4c, the outer cover layer 42 is coextensive with the liquid impervious backsheet 60. The leg elastic material 140 is disposed so as to extend generally longitudinally along the longitudinal side edge 48 of the main body 38. The leg elastic material 140 may be disposed at least in the crotch region 30 of the absorbent article 20 or may be disposed along the entirety of the longitudinal side edge 48.

The outer cover layer 42 comprises a material separate from the material of the inner layer 83 and the outer layer 82 constituting the belt 40. The outer cover layer 42 may comprise two or more layers of materials. The outer cover layer 42 may comprise any known materials and may comprise materials used for the front and back belt 84, 86 as explained above. The outer cover layer 42 may comprise a single layer of nonwoven web of synthetic fibers. The outer cover layer 42 may comprise a single layer of hydrophobic, non-stretchable nonwoven material. The outer cover layer may comprise a film, a foam, a nonwoven, a woven material or the like and/or combinations thereof such as a laminate of a film and a nonwoven.

Test Method:
1. Basis Weight, Initial Tensile Test, and Hysteresis Test
1-1. Sample Preparation The direction in which the elastic laminate will stretch in its intended use is considered the primary stretch direction of the material. One set of rectilinear specimens at least 56 mm long in the primary stretch direction, and 25.4 mm wide in the perpendicular direction is cut from the center portion of the product part. Articles having areas of laminate smaller than 56×25.4 mm are considered to be outside the scope of this method. Five specimens are cut from the same portion of identical products for each set. The basis weight of each specimen is measured. Each set is analyzed by the methods described below. For the Tensile Test and Hysteresis Test, the direction in which specimen has longer dimension is considered the specimen direction of stretching.

1-2. Specimen Weight and Basis Weight

Each specimen is weighed to within ±0.1 milligram using a digital balance. Specimen length and width are measured using digital Vernier calipers or equivalent to within ±0.1 mm. All testing is conducted at 22±2° C. and 50±10% relative humidity. Basis weight is calculated using equation below.

$$\text{Basis Weight}\left(\frac{g}{m^2}\right) = \frac{\text{(Weight of the sample in grams)}}{\text{(Length of the sample in meter)(Width of the sample in meter)}}$$

1-3. Tensile Test Setup

A suitable tensile tester interfaced with a computer such as MTS model Alliance RT/1 with TestWorks 4® software or equivalent is used. The tensile tester is located in a temperature-controlled room at 22° C.±2° C. and 50±10% relative humidity. The instrument is calibrated according to the manufacturer's instructions. The data acquisition rate is set to at least 50 Hertz. The grips used for the test are wider than the sample. Grips having 50.8 mm width may be used. The grips are air actuated grips designed to concentrate the entire gripping force along a single line perpendicular to the direction of testing stress having one flat surface and an opposing face from which protrudes a half round (radius=6 mm, e.g. part number: 56-163-827 from MTS Systems Corp.) or equivalent grips, to minimize slippage of the sample. The load cell is selected so that the forces measured are between 10% and 90% of the capacity of the load cell used. The initial distance between the lines of gripping force (gauge length) is set at 50.8 mm. The load reading on the instrument is zeroed to account for the mass of the fixture and grips.

The specimen is mounted into the grips in a manner such that there is no slack and the load measured is between 0.00 N and 0.02 N. The specimen is mounted in the center of the grips, such that the specimen direction of stretching is parallel to the applied tensile stress.

1-4. Tensile Test

The instrument is set up and the specimen mounted as described in the Tensile Test Setup above. The tensile test is initiated and the specimen is extended at 508 mm/min, with a data acquisition rate of at least 50 Hertz, until the specimen breaks, typically 500-1000% strain. The % strain is calculated from the length between grip lines L, and initial gauge length, $L_o$, as illustrated in FIG. 6A, using the following formula:

$$\% \text{ Strain} = \frac{(L - L_0)}{L_0} \times 100$$

Rupture or breakage is defined as sudden drop in force with small increase in strain. For all samples, Force at 130% strain, Force at break, and % Strain at break are reported.

1-5. Hysteresis Test

The instrument is set up and the specimen mounted as described in the Tensile Test Setup section above, except the gauge length is reduced to 25.4 mm. Data acquisition rate is set to at least 50 Hertz.

The Hysteresis Test method for film specimens involves the following steps (all strains are strains):
(1) Strain the specimen to 50% strain at a constant crosshead speed of 25.4 cm per minute.
(2) Go to 0% strain at a constant crosshead speed of 25.4 cm per minute.
(3) Pull the specimen to 0.127 N force and return to 0% strain with no hold time.
Specimen length at 0.127 N force in step (3) is recorded and used to calculate the % set in the material as below.

% Set=((Length at 0.127 N force−Original Gauge length)/Original Gauge length)×100

Five specimens of each film set are measured, and the arithmetic average is calculated for % Set.

The Percent Recovery is defined from % Set data.

Percent Recovery=100%−% Set.

Materials:

Elastomeric laminates of the present inventions are made using stretch bi-laminates, spandex elastic strands, and adhesive. The stretch bi-laminates are used as outer layer in the examples described below. They are prepared by extrusion lamination as described in patent applications US 2009258210, US 2009264844, and US 2010040826. The bi-laminate M20-0018-3B received from Clopay, USA is used. It is made by extrusion bonding 15 gsm bicomponent nonwoven to 20 gsm elastomeric film. The bi-laminate is activated in machine direction using incremental stretching process. Activation is carried out twice to 3 mm depth of engagement with 2.49 mm activation pitch plate on HSRP (High Speed Research Press) machine as described in U.S. Pat. Nos. 7,062,983 and 6,843,134 issued to Anderson et al.

The bi-laminate material edges in machine direction are held at the same place during dual activation. The dual activation releases 60% strain, i.e. 100 mm material stretches to 160 mm, in the bi-laminate, before it hits force wall, i.e. steep increase in force beyond 60% strain. Force wall is where there is steep increase in force with small increase in % strain, i.e. slope greater than 0.1.

For inner layer, Spandex strands are used. Commercially available "Lycra" at 1100 dtex from INVISTA, USA is used as Spandex strands. Bonding of bi-laminate and strands is carried out using glue sprayed in spiral pattern at ~6 gsm. H2861 glue, commercially available from Bostik, USA is sprayed on Silicone release paper to create glue sheets that can be used later to hand bond spandex strands to bi-laminates.

EXAMPLES

Example 1

Activated bi-laminate cut in 220 mm long in machine direction and 30 mm wide in cross direction, and used as outer layers in the laminate. Bi-laminate in non-strained condition is taped down on flat solid surface with film surface on the open side. Tapes are attached on MD edges of bi-laminate with 200 mm spacing between inside edges of tapes. Spiral glue sheet is applied on top of the film surface, and rolled with HR-100 ASTM roller before removing release paper off. Three spandex strands spaced apart by 6-8 mm are taped at 100 mm distance, and used as inner layer. Strands are stretched 100% strain, i.e. 100 mm distance between tape edges stretches to 200 mm, and are laid over the open glue face of the laminate being made. Strand stretch direction is aligned to laminate machine direction, and center strand is placed at 15 mm from the top edge of the laminate. Strands are held in the stretched condition using tapes at the edges. Another glue sheet is applied on top of the strands and rolled as before. Once, the release paper is removed, another bi-laminate is placed on top of the laminate. The second bi-laminate of the same dimensions as the first bi-laminate, is aligned in Machine direction and cross-direction with the first bi-laminate. Whole laminate assembly is then rolled with HR-100 ASTM roller, and relaxed to allow partial elastic recovery. When relaxed, outer layers adhered on top and bottom of the inner layer are gathered when inner strand layer returns to their original positon. Example 1 represents laminate making described in FIG. 7A, where the strain in the $\varepsilon_b$ of the outer layer bi-laminate, 701, is virtually equal to zero. The inner strand layer has strain of 100%, which is $\varepsilon_s$. The corrugations or puckering is tight as the difference in strain $(\varepsilon_s-\varepsilon_b)$ is high.

Example 2

Figure 9:
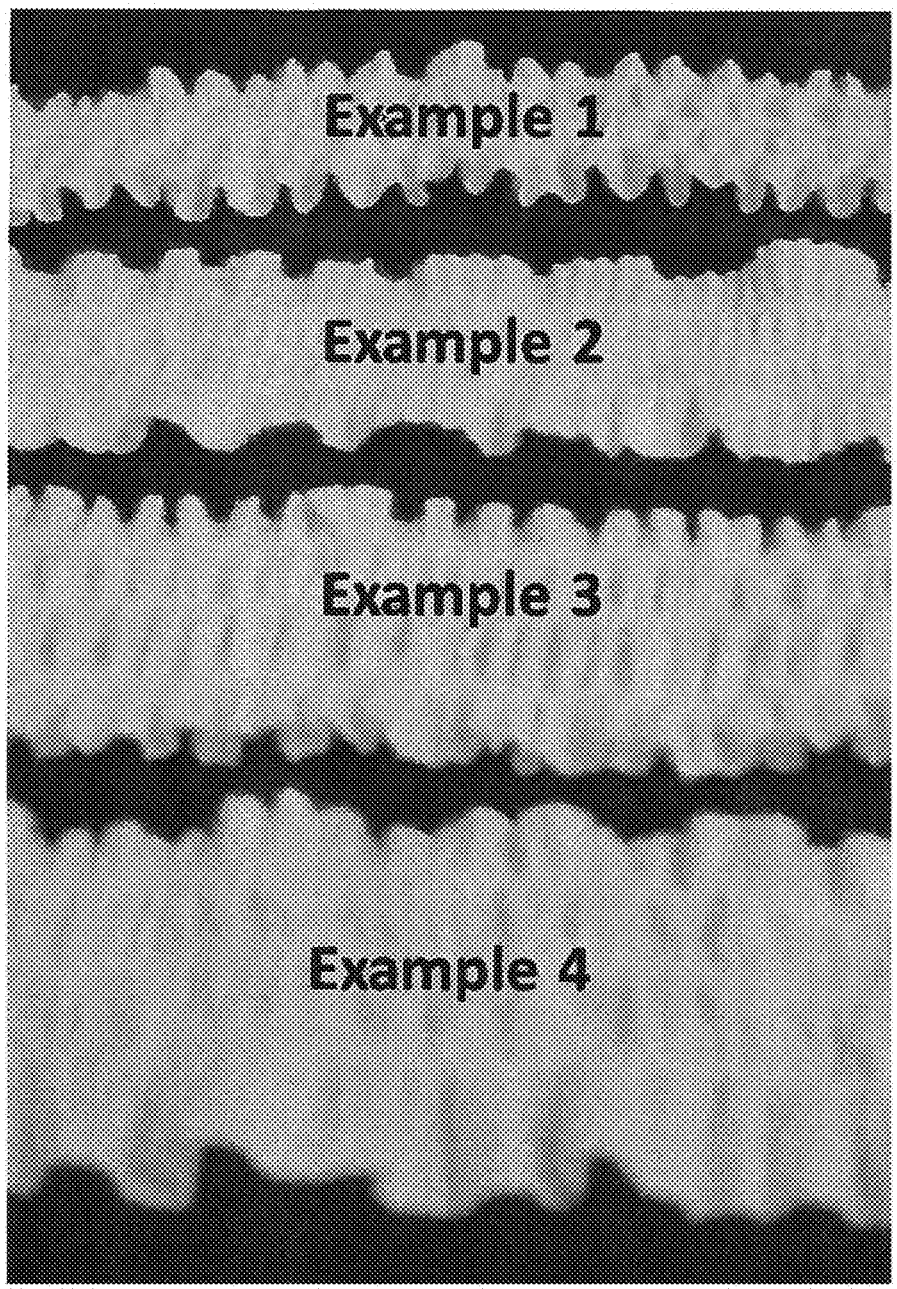
FIG. 9 is a photograph of Examples 1-4.

Example 2 is made the same way as Example 1, except both bi-laminates, first and second, are strained to 60% before combining. When outer layers made of bi-laminate are strained, i.e. $\varepsilon_b$=60%, and the inner layer made of strands is strained to 100%, $\varepsilon_s$=100%, the $(\varepsilon_s-\varepsilon_b)$ value is 40%, in between minimum 0% and maximum 100%. This produces intermediate gathering as shown in FIG. 9.

Example 3

Example 3 is made the same way as Example 1, except elastic strands are stretched to 150% before combining. The difference in strain, $(\varepsilon_s-\varepsilon_b)$, is higher compared to Example 1. This results in tighter gathering compared to Example 1 as shown in FIG. 9.

Example 4

Example 4 is made the same way as Example 2, except elastic strands are stretched to 150% level before combining.

FIG. 9 shows Examples 1-4.

Figure 10:
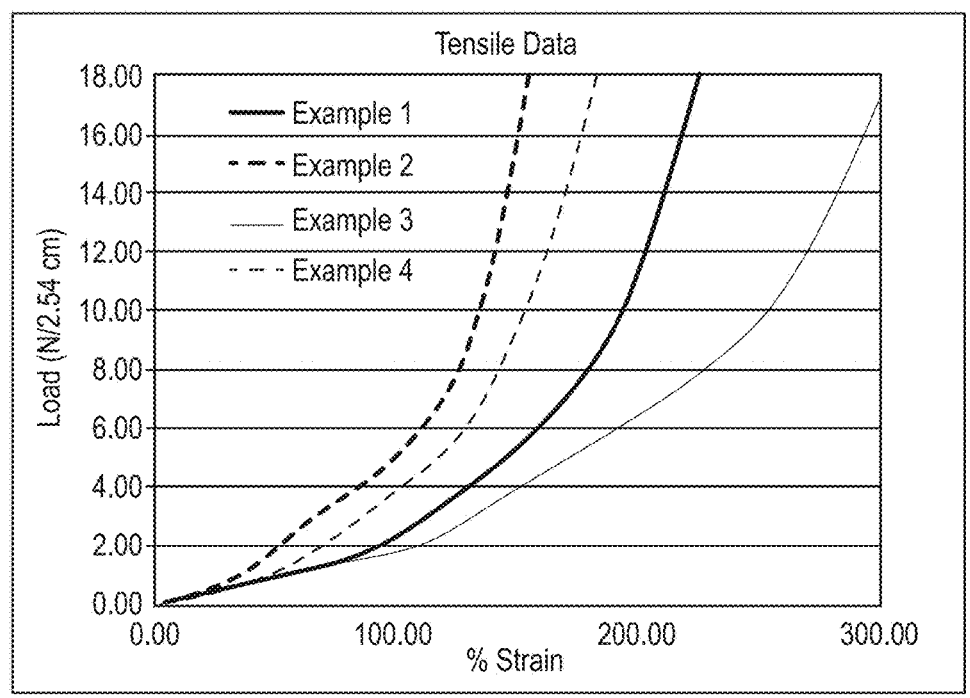
FIG. 10 is a graph of tensile data for Examples 1-4.

The four example materials were tested as per the Tensile Test described above. FIG. 10 shows Force(load)-Strain curve for Example 1 through 4.

Example 1 follows strand force profile until 90% strain, and then follows bi-laminate plus strand combined force profile until it hits force wall at around 180% strain. Although strands were strained to 100%, only 90% strain is achieved in the final laminate as some of the stretch is lost due to resistance from outer layer gathering and glue lamination. The use of stretch bi-laminate instead of non-stretch substrate as outer layer however released additional 90% stretch out of the final laminate. This example shows that stretch level of the laminate of present invention can be tailored by selective combination of inner and outer layers, while keeping combining strain level during lamination process lower.

Example 2 on the other hand was tailored to improve stress or force profile while keeping the laminate stretch level nearly the same as the combining strain. The laminate of example 2 follows strand force profile upto 30% strain, although the strands were strained to 100% during combining. After 30% applied strain, the laminate follows bilaminate plus strand force profile as the force increases with the strain. Eventually at around 120% strain, the laminate hits force wall profile. Such force-strain profile of laminate helps improve product fit when desired.

Example 3 and 4 are variation of Example 1 and 2, respectively. Example 3 and 4 show little higher stretch level compared to Example 1 and 2.

The dimensions and values disclosed herein are not to be understood as being strictly limited to the exact numeral values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   a topsheet;
   an outer cover; and
   an absorbent core disposed between the topsheet and the outer cover;

wherein the outer cover comprises a multilayer substrate comprising:
  a first outer layer and a second outer layer, wherein at least one of the first and second outer layers comprises a component that exhibits at least partial elastic recovery after mechanical activation in the machine direction;
  an inner layer, disposed between the first outer layer and the second outer layer, the inner layer comprising elastic strands; and
  wherein at least one of the first outer layer and second outer layer is laminated to the inner layer; and
  wherein at least one of the first and second outer layers comprises a film comprising at least one elastomeric component.

2. The absorbent article of claim 1, wherein the inner layer comprising elastic strands is prestrained.

3. The absorbent article of claim 1, wherein at least one elastomeric component is a polyolefin.

4. The absorbent article of claim 1, wherein at least one of the first and second outer layers comprises a multilayer nonwoven structure comprising at least one elastomeric component.

5. The absorbent article of claim 1, wherein at least one of the first and second outer layers that is mechanically-activated in the machine direction is prestrained.

6. The absorbent article of claim 1, wherein the inner layer and the at least one of the first and second outer layers that exhibits at least partial recovery after mechanical activation in the machine direction are each prestrained prior to being bonded to one another.

7. The absorbent article of claim 6, wherein the amount of prestraining of the at least one of the first and second outer layers is the same as the amount of prestraining of the inner layer.

8. The absorbent article of claim 6, wherein the amount of prestraining of the at least one of the first and second outer layers is less than the amount of prestraining of the inner layer.

9. The absorbent article of claim 6, wherein the multilayer substrate is defined in the x-y plane and wherein the at least one of the first and second outer layers expands in the z-direction upon recovery in the machine direction.

10. The absorbent article of claim 9, wherein the expansion in the z-direction upon recovery in the machine direction increases with an increase in the differential in the percent recovery between the at least one of the first and second outer layers and the inner layer.

11. The absorbent article of claim 9, wherein the differential in the percent recovery between the at least one of the first and second outer layers and the inner layer is about zero.

12. The absorbent article of claim 9, wherein the percent recovery of the at least one of the first and second outer layers is about zero.

13. The absorbent article of claim 1, wherein the inner layer and at least one of the first or second outer layers are bonded to one another prior to the multilayer substrate being mechanically activated in the machine direction.

14. The absorbent article of claim 1, wherein at least one of the first or second outer layers is mechanically activated in the cross direction prior to being activated in the machine direction.

15. The absorbent article of claim 1, wherein the at least one of the first and second outer layers that exhibits at least partial elastic recovery after mechanical activation in the machine direction comprises a multilayer nonwoven comprising at least one meltblown layer.

16. The absorbent article of claim 15, wherein the at least one meltblown layer comprises an elastic component.

17. The absorbent article of claim 1, wherein the at least one of the first and second outer layers that exhibits at least partial elastic recovery after mechanical activation in the machine direction comprises a film and nonwoven laminate structure.

18. The absorbent article of claim 1, wherein the inner layer comprises an elastomeric polyolefin or a styrenic block copolymer.

19. The absorbent article of claim 1, wherein the multilayer substrate comprises from about 1 gsm to about 10 gsm of adhesive.

20. The absorbent article of claim 1, wherein at least one of the first and second outer layers comprises a film and nonwoven laminate, wherein the film comprises discrete film strips.

21. The absorbent article of claim 1, wherein the multilayer substrate is activated in the cross direction.

22. The absorbent article of claim 1, wherein the multilayer substrate is mechanically activated in at least two directions.

23. The absorbent article of claim 1, wherein the at least one of the first outer layer and second outer layer is laminated to the inner layer while in a stretched state.

24. An absorbent article comprising:
  a topsheet;
  an outer cover; and
  an absorbent core disposed between the topsheet and the outer cover;
  wherein the outer cover comprises a multilayer substrate comprising:
    a first outer layer and a second outer layer, wherein at least one of the first and second outer layers comprises a component that exhibits at least partial elastic recovery after mechanical activation in the machine direction;
    an inner layer, disposed between the first outer layer and the second outer layer, the inner layer comprising elastic strands; and
    wherein at least one of the first outer layer and second outer layer is laminated to the inner layer; and
    wherein at least one of the first and second outer layers comprises a film-nonwoven laminate.

25. An absorbent article comprising:
  a topsheet;
  an outer cover; and
  an absorbent core disposed between the topsheet and the outer cover;
  wherein the outer cover comprises a multilayer substrate comprising:
    a first outer layer and a second outer layer, wherein at least one of the first and second outer layers comprises a component that exhibits at least partial elastic recovery after mechanical activation in the machine direction;
    an inner layer, disposed between the first outer layer and the second outer layer, the inner layer comprising elastic strands; and
    wherein at least one of the first outer layer and second outer layer is laminated to the inner layer; and
    wherein at least one of the first and second outer layers comprises a low-melting elastomeric material.

* * * * *